US00PP35718P2

(12) United States Plant Patent
Ruckle et al.

(10) Patent No.: US PP35,718 P2
(45) Date of Patent: Apr. 2, 2024

(54) ***CANNABIS* PLANT NAMED 'PURE RED 3'**

(50) Latin Name: ***Cannabis* Hybrid**
Varietal Denomination: Pure Red 3

(71) Applicant: Puregene AG, Zeiningen (CH)

(72) Inventors: Michael Eduard Ruckle, Winterberg (CH); Maximilian Moritz Vogt, Zurich (CH)

(73) Assignee: Puregene AG, Zeiningen (CH)

( * ) Notice: Subject to any disclaimer, the term of this patent is extended or adjusted under 35 U.S.C. 154(b) by 0 days.

(21) Appl. No.: 18/077,970

(22) Filed: Dec. 8, 2022

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
CPC ..... A01H 5/02
See application file for complete search history.

*Primary Examiner* — Kent L Bell
(74) *Attorney, Agent, or Firm* — Knobbe, Martens, Olson & Bear, LLP

(57) ABSTRACT

A new and distinct *Cannabis* plant named 'Pure Red 3' is characterized by its unique pungent strawberry aroma that is distinct and clearly recognizable. 'Pure Red 3' has a high flower to biomass ratio and a relatively short flowering time compared with other commercial varieties known to the inventors.

11 Drawing Sheets

Specification includes a Sequence Listing.

Latin name of the genus claimed: *Cannabis* Hybrid.
Variety denomination: 'PURE RED 3'.

REFERENCE TO ELECTRONIC SEQUENCE LISTING

The present application contains an Electronic Sequence Listing, which is provided as a file entitled PCR008PSEQLIST.xml, which is 130,228 bytes in size, and which was created on Apr. 4, 2023, which is replaced by a Replacement Electronic Sequence Listing submitted as a file entitled PCR008PREPLACEMENTSEQLIST.xml, which is 130,059 bytes in size and was created on Jul. 19, 2023. The information in the Electronic Sequence Listing is incorporated herein by reference in its entirety.

BACKGROUND AND SUMMARY OF THE INVENTION

A novel *Cannabis* hybrid cultivar, named 'Pure Red 3' is provided. 'Pure Red 3' is the result of a planned breeding program and originated from crosses between the pollen donor (male) 'Amnesia Haze' (unpatented) and the pollen acceptor (female) 'Strawberry Haze' (unpatented). The new cultivar has been vegetatively reproduced by cloning using stem cuttings at Zeiningen, Switzerland. Vegetative clones of 'Pure Red 3' were tested in controlled greenhouses, and outdoors in open fields. The desired characteristics of each source cultivar are transferred by vegetative, asexual reproduction. 'Pure Red 3' is stable and consistently true-to-type through multiple generations of vegetative reproduction.

*Cannabis* is a genus of flowering plants comprising three historically distinct subspecies based on phenotype and metabolite profiles—*Cannabis sativa, Cannabis indica,* and *Cannabis ruderalis*. However, decades of crossing and selection makes it impossible to absolutely characterize the resulting hybrid plants using phenotypic data. Most of the *Cannabis* varieties being sold for medicinal and recreational purposes contains characteristics of both *Cannabis sativa* and *Cannabis indica* subspecies. For this reason, 'Pure Red 3', described herein, has been characterized both on the presented phenotype, as well as the genotype using a series of single nucleotide polymorphisms (SNPs).

Used herein, the terms "cultivar", "variety", "clone" and "strain" are used interchangeably.

*Cannabis* plants synthesize unique terpeno-phenolic compounds in varying concentrations. High genetic variability has resulted in the vast varieties of chemotypes with distinct characteristics available today. More than 500 unique compounds including cannabinoids, terpenoids, terpenes, flavonoids, amino acids, vitamins among many others, are secreted as a sticky resin by the glandular trichomes found on the floral calyxes of female plants. Cannabinoids and terpenes are the biologically active chemicals responsible for the pharmacological and psychoactive properties of *Cannabis* when consumed by humans. They often work together synergistically in what is commonly known as the "entourage effect" and as such, small differences in composition or concentration any of these compounds can have notable effects on the physiological effect of consumed or applied *Cannabis* in or on the human body.

Cannabinoids are produced at significant concentrations in *Cannabis*. Although over a hundred cannabinoids have been identified in *Cannabis* , the major cannabinoids include, Δ9-tetrahydrocannabinol (THC), cannabidiol (CBD), cannabigerol (CBG), cannabinol (CBN), cannabichromene (CBC), cannabinodiol (CBDL), cannabicyclol (CBL), cannabivarin (CBDV), cannabigerovarin (CBGV), cannabichromevarin (CBCV), tetrahydrocannabivarin (THCV), cannabidivarin (CBDV), cannabigerol monomethyl ether (CBGM), cannabilsoin (CBE), cannabicitran (CBT), cannabinol propyl variant (CBNV), cannabitriol (CBO), tetrahydrocannabinolic acid (THCA), tetrahydrocannabivarinic acid (THCVA), cannabidiolic acid (CBDA), cannabigerolic acid (CBGA) and cannabinerolic acid. These cannabinoids are usually produced by the plant in their acid form (see suffix-A), but upon heating they become decarboxylated.

Terpenes are organic molecules produced by various plants and animals. These organic compounds are responsible for the strong and distinctive smell and taste of *Cannabis*. Some of the most prominent terpenes found in *Cannabis* are myrcene, caryophyllene, and limonene, to mention a few.

The objective of the breeding program that produced 'Pure Red 3' was to develop *Cannabis* plant varieties with a unique aroma as well as unique combinations of cannabinoids and/or terpenes, while displaying a phenotype with multiple large inflorescences arranged in a naturally branched habit. The variety described herein is a result of this breeding program.

The 'Pure Red 3' cultivar was the result of a cross between 'Amnesia Haze' and 'Strawberry Haze' *Cannabis* plants. Selected progenies were then cloned and crossed by selfing using methods known in the art. In subsequent generations, the resultant plants were screened for unique and strong fruit aromas and selected based on production-relevant phenotypes. The progeny with the most stable desirable aroma, production quality, and chemotype was assigned the name, 'Pure Red 3'.

The 'Pure Red 3' plants described herein were grown both in nurseries, climate-controlled growth facilities in Zeiningen, CH, 4314 (47°32'53.5"N 7°51'53.2"E), and in the field in Niederwil, CH (47°22'49.9"N 8°18'12.6"E) during the 2022 season. Samples for metabolite analysis were taken from the flowers of numerous plants. Analytical measurements were made using Ultra Performance Liquid Chromatography by those skilled in the art. Plant phenotyping was performed using photography and subsequent analysis.

The 'Pure Red 3' variety described herein has a pungent strawberry aroma that is clearly recognizable. The aroma provides a pleasant sensory experience that is appealing to the consumer and therefore adds value to the flower as a commercial product. It furthermore has a high flower to biomass ratio and a relatively short flowering time compared with other commercial varieties.

Freeze-dried flowers from 'Pure Red 3' plants were analyzed at harvest from both greenhouse and outdoor growth environments. The terpene profiles were acquired using ethanolic extraction and HPLC methods well known to those skilled in the art. The resultant terpene content was 1.049 (% w/w) with beta-myrcene, beta-caryophyllene and bisabolol being the dominant terpenes (Table 1). The unique terpene profile has been shown not to be correlated with the unique smell of 'Pure Red 3'.

'Pure Red 3' has a cannabinoid profile in the dried mature female flowers that is dominant in total CBD (12.69 w/w) with total THC (0.57% w/w), total CBC (0.72% w/w) and total CBG (0.17% w/w) (Table 1).

TABLE 1

Terpene (left column) and Cannabinoid (right column) profiles of 'Pure Red 3' mature flowers

| Terpene | 'Pure Red 3' [% w/w] | Cannabinoid | 'Pure Red 3' [% w/w] |
|---|---|---|---|
| caryophyllene oxide | 0.009 | CBD | 0.35 |
| beta-pinene | 0.014 | CBDA | 14.07 |
| D-limonene | 0.015 | Total CBD | 12.69 |
| linalool | 0.026 | CBG | 0.05 |
| fenchol_bornylacetate | 0.03 | CBGA | 0.14 |
| alpha-eudesmol | 0.03 | Total CBG | 0.17 |
| beta-eudesmol | 0.039 | d9-THC | 0.04 |
| alpha-pinene | 0.045 | d8-THC | 0 |
| alpha-humulene | 0.046 | THCA | 0.6 |
| All-E-Beta-farnesene | 0.051 | Total THC | 0.57 |
| selina-3,7(11)-diene | 0.078 | CBC | 0.03 |
| beta-ocimene 2 | 0.079 | CBCA | 0.78 |
| guaiol | 0.086 | Total CBC | 0.72 |
| bisabolol | 0.133 | CBN | 0 |
| beta-caryophyllene | 0.161 | CBDV | 0 |
| beta-myrcene | 0.209 | CBDVA | 0.02 |
| Total terpene content (% w/w) | 1.049 | Total CBDV | 0.02 |

The genotype of 'Pure Red 3' was characterized using genotyping-by-sequencing (GBS). Short-read sequencing data produced by this method were aligned to the publicly available assembled genome of cs10 (Assembly: GCF_900626175.1) to identify single nucleotide polymorphisms (SNP) and short haplotypes (HAP, a combination of linked SNPs) in 'Pure Red 3' (Table 2 and FIG. 11). Together these polymorphisms provide a fingerprint which can be used to differentiate 'Pure Red 3' from all other *Cannabis* varieties known to the inventors.

Table 2 shows a list of single nucleotide polymorphisms (SNPs) and haplotypes (HAPs) contained within the genome of 'Pure Red 3' compared to the publicly available reference genome of cs10 (Assembly: GCF_900626175.1). Each record shows the reference chromosome of cs10, the nucleotide position on the cs10 reference sequence, the nucleotide sequence at this position, the nucleotide sequence displayed in 'Pure Red 3', and whether the state of the polymorphism is homozygous or heterozygous in 'Pure Red 3'. Heterozygous loci contain one allele sequence identical to the reference nucleotide sequence and one allele of the 'Pure Red 3' sequence.

TABLE 2

| Chromosome | Position | [Reference\|'Pure Red 3'] | State |
|---|---|---|---|
| NC_044370.1 | 2779345 | TTATCGTTTTTTTGGTTTTTGATA[G\|A]ATCACACAAATCATTGTATTTATCC (SEQ ID NO: 1) | homozygous |
| NC_044370.1 | 2780081 | TAAAAATAGAAAGAAAGACCATTC[C\|T]AAGAATAATTTTTTTTTATGCATTT (SEQ ID NO: 2) | homozygous |

TABLE 2-continued

| Chromosome | Position | [Reference\|'Pure Red 3'] | State |
|---|---|---|---|
| NC_044370.1 | 3365760 | AGGCTTTAAGGTAATACTAATACA[T\|C]GAGGCATAAATATAAAACTGACAGC (SEQ ID NO: 3) | homozygous |
| NC_044370.1 | 3367067 | TGTTGGATCATGAGCTGAATTTCT[T\|A]ATTTCATTAGCAGAAGGAAACATAG (SEQ ID NO: 4) | homozygous |
| NC_044370.1 | 3367795 | TCTCACTTTTTCCCACAATACCAC[C\|T]AGAGTTTCCAGATGAGGTTCCACCA (SEQ ID NO: 5) | homozygous |
| NC_044370.1 | 3369013 | AAACAATTGCAACTCTCACAATTT[C\|G]AGCGTTCAGATTTGGCACCAAAATT (SEQ ID NO: 6) | homozygous |
| NC_044370.1 | 23296332 | AATAATTATTAAAAATTAACTTTC[A\|C]TAAACCAAATACCAAAATATTTAAA (SEQ ID NO: 7) | heterozygous |
| NC_044370.1 | 23736190 | AAATTTTACTTTTAGGTATACACA[G\|A]TAGTTATTCAATTGGTATTTAACGA (SEQ ID NO: 8) | heterozygous |
| NC_044370.1 | 62225828 | TACCTAGTTCGGAAGGCTGTCTTC[G\|C]GGATATCCTCTTCTCGAATTCTCAA (SEQ ID NO: 9) | homozygous |
| NC_044371.1 | 71183277 | AGATAGATCTCCCACACATATATA[C\|T]AGTATTTTTGTTTTAGTTTTCACTT (SEQ ID NO: 10) | homozygous |
| NC_044371.1 | 71188411 | TTTGTTGTGCAAAGAATACATTTT[C\|T]TAAGTTTAAGGCCACACCATCATGT (SEQ ID NO: 11) | homozygous |
| NC_044371.1 | 75274212 | CTCTAAAAACTTCCTCTGGATATA[G\|A]TCCTTTGACCGAACTTGTTAAAGAA (SEQ ID NO: 12) | homozygous |
| NC_044371.1 | 75275206 | CAGTAGCAATGTAATAGGAGAAAT[A\|G]CAAAGAAACACCTTGAGCTCAAAAA (SEQ ID NO: 13) | homozygous |
| NC_044371.1 | 80905221 | TGTGTAGCAAATGCTTTAATATTG[A\|C]CATCCGATTGGGTTACTGATTCGAT (SEQ ID NO: 14) | homozygous |
| NC_044371.1 | 80905381 | CCATCTCAGGAAATTGGAAGATTC[T\|C]TCAAACAACCTGTATTAATTGTTCC (SEQ ID NO: 15) | homozygous |
| NC_044371.1 | 84135656 | CGAAAAACTAAAAACATCCCAATT[C\|A]AAATATCAACAACAGTAATTCTAAT (SEQ ID NO: 16) | heterozygous |
| NC_044371.1 | 89882687 | GTACTTTCAATACTGCCTCCAAGA[C\|T]GCCAAATAAGTATTTGAGTTTTTTT (SEQ ID NO: 17) | homozygous |
| NC_044371.1 | 91003402 | TCTTTATTGGTTTGTCACACTTGT[G\|A]GTTCGGTGGAATCCCGTATATCGTC (SEQ ID NO: 18) | homozygous |
| NC_044371.1 | 91472889 | TTGTAATTGAAAACAATTAGAAAC[C\|T]TAACCTTGGAGCCTATTCAGGCATA (SEQ ID NO: 19) | homozygous |
| NC_044371.1 | 91698319 | GAATTTAGAGATGTTATTGGATCC[G\|A]CTGCTTTCTGTTGAACCTTTTAACT (SEQ ID NO: 20) | homozygous |
| NC_044371.1 | 91734682 | CCATGGCGCTGGCGTTTGTCATGA[G\|C]TACTGTCTTGTGGCTCTTCATGCCT (SEQ ID NO: 21) | homozygous |
| NC_044372.1 | 3370925 | GTACCTTTTTCTCTGAATGAAAAT[T\|G]TGAAATTTACAATATAACTCAATAA (SEQ ID NO: 22) | heterozygous |
| NC_044372.1 | 8063254 | ACCCTATAGTATTATTTACTTATG[C\|A]CATAAAAAAGTAAATTATACCCTCA (SEQ ID NO: 23) | homozygous |
| NC_044373.1 | 8638211 | GACTTGTCAATAACATAAATTCAT[A\|G]TTTGCATTAGATATTTGCATATATT (SEQ ID NO: 24) | heterozygous |
| NC_044373.1 | 19751564 | AGGTTGATGCAGATTAATCTCCAA[C\|T]CTTAAAAATTGGCAGTAATAGTCTC (SEQ ID NO: 25) | heterozygous |
| NC_044373.1 | 38582963 | TAACAGTTTTTAAATGCATTAACC[C\|T]AAAATAGTTAGAATTCATGTCAAGT (SEQ ID NO: 26) | heterozygous |
| NC_044373.1 | 38884733 | TGACGCCGGAAAAATTGTCGGAGT[T\|C]GCTGCCAACGCTGGAAAATTCTGAC (SEQ ID NO: 27) | heterozygous |

TABLE 2-continued

| Chromosome | Position | [Reference\|'Pure Red 3'] | State |
|---|---|---|---|
| NC_044373.1 | 73450097 | ACCAGAAGCAAAGAATAGCATGTC[A\|G]TATTCATATGGATATATTATTTGAA (SEQ ID NO: 28) | heterozygous |
| NC_044373.1 | 76955564 | GGCAAATGTCTAAATAGTTCTAGC[T\|G]AACCAATAATACAGTAGTCAAACAG (SEQ ID NO: 29) | heterozygous |
| NC_044373.1 | 85245050 | CTAGCTGCCATTGGGGTTGATGGA[T\|C]CTAATTCAATCTTTCCCATTGCATA (SEQ ID NO: 30) | homozygous |
| NC_044374.1 | 798175 | TCTCACAGTTCCCTTACCAAAATA[A\|T]ATATAAGGAAAAGTGTTTTGACATC (SEQ ID NO: 31) | homozygous |
| NC_044374.1 | 1336157 | GGTATATATATAATACTTTTTCTA[C\|G]TCCTTTATATTCACATAATTAACAA (SEQ ID NO: 32) | homozygous |
| NC_044374.1 | 1338351 | AAAAAAAAAAACAGTATAAGATAC[T\|C]TGGTTACCCTTTATGGTAACTGGTT (SEQ ID NO: 33) | homozygous |
| NC_044374.1 | 1489943 | ACTCATGGGTTTAGAAAAGGGATA[A\|T]TTACATAAGACATCATCTTTTGTAA (SEQ ID NO: 34) | heterozygous |
| NC_044374.1 | 1937685 | TCTTTTTATTCGTTTCGGATCTAG[C\|T]GTTTTGCAAAAGTTACAGATTAAAC (SEQ ID NO: 35) | homozygous |
| NC_044374.1 | 1954572 | TGTGCGGATTCCTTTATCTATCTT[G\|T]TCGTAATTGAATAGCAGTTACAATA (SEQ ID NO: 36) | homozygous |
| NC_044374.1 | 2087265 | GAAAAATCCTGGTGTTGTTCTTTG[C\|T]AATCTTGATTTTGTGTGTTTGAATT (SEQ ID NO: 37) | homozygous |
| NC_044374.1 | 2196975 | TATCAAAGCTTAAACGGAATAATA[A\|C]GGTTTTAGTAATTGAATAAATAATA (SEQ ID NO: 38) | homozygous |
| NC_044374.1 | 2316953 | GACTCCTCCCTTTTCTCTTGGAAC[C\|A]ATAGAAATAAGAAATTGGAACTTAG (SEQ ID NO: 39) | homozygous |
| NC_044374.1 | 2582077 | ATCACTGGGTCAGATCAAATGATT [A\|C]AAAAACAAAATCAAAATTTTCTACT (SEQ ID NO: 40) | homozygous |
| NC_044374.1 | 2585275 | AGAAATAACATGTATAAGGCAAGT[T\|A]AAGGAAAAGTACCTGTTCCTCCATC (SEQ ID NO: 41) | homozygous |
| NC_044374.1 | 2624579 | TCATATAAGTTTGCTTTGACTTTT[C\|T]ATTGATCTCTTATGCAAATTATTAG (SEQ ID NO: 42) | homozygous |
| NC_044374.1 | 2816373 | AAGCCCAATTAACCACATTATGGG[T\|C]TGCAAAATTACAAGTTCTACTAACA (SEQ ID NO: 43) | heterozygous |
| NC_044374.1 | 11969153 | CTTGACAAAGAGTTTCATTGTCTT[T\|G]TTGGGAAAAGGTAGAAATCTGCCTT (SEQ ID NO: 44) | heterozygous |
| NC_044374.1 | 80183156 | AACTTCATTATAAGAAAAGTCATT[A\|G]TACTTAGAATCTCTGAAACATAAGT (SEQ ID NO: 45) | heterozygous |
| NC_044374.1 | 85682798 | CATTTGAGTGAGAAAATCCTCAAA[T\|G]TGAGGAAAGTTGTCATGCATGATCA (SEQ ID NO: 46) | homozygous |
| NC_044374.1 | 85686797 | TTCACTTTGGCCATGACAAGCATA[G\|A]CTAGTCAATAAAGTATTCCAAGAAA (SEQ ID NO: 47) | homozygous |
| NC_044374.1 | 85688608 | TATTTAAATATTATTTTCATATTA[C\|T]TTTTATGTAATTTTCTTGTTGTTTT (SEQ ID NO: 48) | homozygous |
| NC_044374.1 | 85689554 | ACACTTTCTAGGAAAACTTCTCAA[G\|A]AAGCCACCCATTCTTTCGTCAGAGT (SEQ ID NO: 49) | homozygous |
| NC_044374.1 | 85690316 | CAGTGCGGCTGACCTGAGGTGTAT[A\|G]ACTACGCTTGCCAATTAGGATATTT (SEQ ID NO: 50) | homozygous |
| NC_044374.1 | 86041975 | ATTTTCTTCGTCTTCTTTCACAAA[C\|T]GGAAGGCTGCCGGGGCTTTCTTCCT (SEQ ID NO: 51) | homozygous |
| NC_044374.1 | 86073753 | CAATTTTTTCAATTGAAGCGGTTT[C\|A]ACGTGTTTGATGTTTTGGATGCATT (SEQ ID NO: 52) | homozygous |

TABLE 2-continued

| Chromosome | Position | [Reference\|'Pure Red 3'] | State |
|---|---|---|---|
| NC_044375.1 | 5022563 | GGCCAAGGCTCCATATGAGAGCCA[T\|G]GAGCAATGGAAAAAATTTATATATA (SEQ ID NO: 53) | heterozygous |
| NC_044375.1 | 18112288 | ACTAGGAGATACTGCAGTTAGTCT[C\|G]AATACAGTTGAAGTGGAATAGGTAG (SEQ ID NO: 54) | homozygous |
| NC_044375.1 | 28641765 | AACCTCTCCCAGGGTCAGCCTGAT[C\|A]CTGATGTTTGAGGGAAGGGTTTGGC (SEQ ID NO: 55) | heterozygous |
| NC_044375.1 | 36437352 | ATTTGATTCAATGTCTAATAACTC[A\|T]GGTGATTTTTTATGCCATTCTTAGG (SEQ ID NO: 56) | homozygous |
| NC_044375.1 | 37785288 | TTATAGCAATTAATATATGGTTTA[A\|G]AAACAGTGAATATTAAATATTAATA (SEQ ID NO: 57) | homozygous |
| NC_044375.1 | 42426619 | AAAATGATCATTAAACCATATCTA[A\|G]CCCATCAGACTCGCTCTCCCTGCTG (SEQ ID NO: 58) | homozygous |
| NC_044375.1 | 47326075 | GACCGCCTCCCATCTCGACCCTAT[T\|G]ACCCTGACTCCTTGTATTTCGTTGG (SEQ ID NO: 59) | heterozygous |
| NC_044375.1 | 49450673 | CAACCCAGAACAACTTAAGAGTCA[G\|A]TATAAGCAAGAATTCAAACACAAAA (SEQ ID NO: 60) | homozygous |
| NC_044375.1 | 55873504 | TACACTTCATTTTATAAATGATAA[A\|G]ACTGTAGAAACAATTGAAATTTAGA (SEQ ID NO: 61) | homozygous |
| NC_044375.1 | 68632328 | ATCAAGCTAAATGGGAAAACTTCC[T\|C]ACAATAGAAATCAAGCAATTAATTC (SEQ ID NO: 62) | homozygous |
| NC_044375.1 | 73790821 | AGGAAATAGTACAAAAGATTTAAT[G\|A]AATATGTACTGAAAATTAATTTCAG (SEQ ID NO: 63) | homozygous |
| NC_044375.1 | 80529927 | TCAAACAACATTCAATCTGTACAA[G\|A]TGCATATTTTAGATTTTTCAATCCA (SEQ ID NO: 64) | heterozygous |
| NC_044375.1 | 81925670 | TTATTTAGCCCTAATATTATTAAT[A\|G]TAGTTACTGCTGTTATATGGGGATA (SEQ ID NO: 65) | homozygous |
| NC_044375.1 | 82781503 | ATTCATCCAAAACTTCCTAATCCC[C\|TJAAAAGAACCGAATGAATCAATTGTG (SEQ ID NO: 66) | heterozygous |
| NC_044375.1 | 92297823 | TAGCAAGCAAAGCATCTTGGTCAT[A\|G]TAAAAAAATCACCACATAGCAAAAG (SEQ ID NO: 67) | homozygous |
| NC_044375.1 | 92620160 | ATAGGGACATCATCTATAATAGTG[G\|T]GTATCTCTTAAAGAAAATGAAAATA (SEQ ID NO: 68) | homozygous |
| NC_044375.1 | 93919996 | TATTTCAGCAAAAAAGAACATATA[G\|A]TTTTAGTAGCAGGATCAACCCTGAG (SEQ ID NO: 69) | homozygous |
| NC_044375.1 | 96097440 | ATTTAATAATGTAAAATGATATTA[A\|C]ACTATAAGTTATATTTGTATAGGTT (SEQ ID NO: 70) | homozygous |
| NC_044376.1 | 1752643 | TGACTGTGCAGCATAGCTTATGAA[C\|A]TATCAAGAGTGTTAGGATCCCACTC (SEQ ID NO: 71) | heterozygous |
| NC_044376.1 | 26328689 | GGGACATTGAGGAGATGATGAAAT[G\|A]TGGCGATATTGCAAAATAGCAGCAG (SEQ ID NO: 72) | homozygous |
| NC_044376.1 | 34067962 | TATTTTTTCAGAACTGATTGTGGC[A\|G]TTTACCTCATCAAATTTGTTGAATT (SEQ ID NO: 73) | homozygous |
| NC_044377.1 | 56383869 | AGCGAGGAGATATATCAGATGCAA[A\|C]GGTCTAAAGGTTTGTTTACCATCTC (SEQ ID NO: 74) | homozygous |
| NC_044377.1 | 56384684 | TCTGATTATATTATGTACTTATTG[C\|T]TTTGGTGTCAAATGACTCTTCCGAT (SEQ ID NO: 75) | homozygous |
| NC_044377.1 | 56385750 | TAAGTTGGGCTTTATCTTTCTATT[T\|G]GAATATTCTGTAAGGTTCTAGATAC (SEQ ID NO: 76) | homozygous |
| NC_044377.1 | 56385885 | ATACAAATTAGTTACTGGCAGAGG[A\|G]ATTTCAAATTGAGACAAGGAGAATT (SEQ ID NO: 77) | homozygous |

TABLE 2-continued

| Chromosome | Position | [Reference\|'Pure Red 3'] | State |
|---|---|---|---|
| NC_044377.1 | 69992291 | AGTCTCGATCTCTCCCTCGAACTA[T\|C]AAAAATCATTGTAAATATCGCCTTC (SEQ ID NO: 78) | heterozygous |
| NC_044377.1 | 69993064 | TCATATTAATTTAGTCACAAAAAA[T\|A]TTATGTTGTAATTAAAAGTAGCCTT (SEQ ID NO: 79) | heterozygous |
| NC_044377.1 | 71077657 | TTTCACCGAAAAGTGAAGATCGAC[T\|C]TCCATTAAGTTTTCAACTTCCTGCA (SEQ ID NO: 80) | heterozygous |
| NC_044377.1 | 71079432 | ATACCATTCAAGATATCTAAGCTC[A\|T]GAAGGAAATGATCAGTCTAGACCAT (SEQ ID NO: 81) | heterozygous |
| NC_044377.1 | 71079717 | CTTGTAACTAAATATGATTTTTAG[C\|T]CACAACAAAAAATTACTTGTAACTA (SEQ ID NO: 82) | heterozygous |
| NC_044377.1 | 73047617 | TGATCTGAGGGCCACTGGGAGGTC[T\|A]CCCATTTGAACTACTACGGCCAAAA (SEQ ID NO: 83) | heterozygous |
| NC_044377.1 | 75536995 | CAATTATTTGAGTCAATAATCAAG[G\|C]TGCAACTGCTCTTAAGCTACCGATC (SEQ ID NO: 84) | homozygous |
| NC_044377.1 | 78400247 | AAATCTTTCAAACACTTGAGGAAG[G\|C]ATCTCAATCATATTAAATATCTATA (SEQ ID NO: 85) | heterozygous |
| NC_044378.1 | 1831436 | AAATTTAATGACCTGGACTAATTA[G\|C]GAACTGCCGCGTGGCTATTGACTTC (SEQ ID NO: 86) | heterozygous |
| NC_044378.1 | 2422567 | CTGTAATTATGTCTAGAGTAAATG[C\|G]TTGTGGATGAGTATGCAATTGATAA (SEQ ID NO: 87) | heterozygous |
| NC_044378.1 | 68164073 | CACTCTGTCATTCCAAACACTAAC[T\|C]CCGGTTCTATGCAGCATCCTCCCGA (SEQ ID NO: 88) | homozygous |
| NC_044378.1 | 69267545 | GAAATCCATTAATAGTAAATGCAT[C\|T]CAATCTAGGATGTGCATCTTTAGAG (SEQ ID NO: 89) | homozygous |
| NC_044379.1 | 27221127 | TGATTCGCTAAGGAATGTTTTGGC[A\|T]TCGCTATGGCGTCCAGGGAGAGGAA (SEQ ID NO: 90) | homozygous |
| NC_044379.1 | 27221390 | ATCGTGTCTTACAAGGCGTGGGAG[C\|G]GTATATTGGAACGTATGTTTTCTCA (SEQ ID NO: 91) | homozygous |
| NC_044379.1 | 27221615 | GCCATTCCGAAAGATTTTGCCACA[G\|A]ATTGTTTGAGGAGTCCTTGGAAACT (SEQ ID NO: 92) | homozygous |
| NC_044379.1 | 27222807 | TGACATGGAGCTAAGGGGTTATCC[A\|T]TTTACTTGGGAAAAAGGGAAGGGTA (SEQ ID NO: 93) | homozygous |
| NC_044379.1 | 27226081 | GATAAAAAAGAAAGGTTGGATTGG[A\|T]ACAATTGTTGAAACCGATTGTCTAA (SEQ ID NO: 94) | homozygous |
| NC_044379.1 | 35641028 | CTTAACATAGGAAGATTCAAATAA[A\|G]TCTTTACCAGATAGAATAAAACCTC (SEQ ID NO: 95) | homozygous |
| NC_044379.1 | 45180313 | CACATTTAGCTGCACGAAATTGAT[A\|G]ATGAACAATAAAAATCAGAATTACA (SEQ ID NO: 96) | homozygous |
| NC_044379.1 | 46956607 | AACCAAAAAGATTACAGACATCCA[C\|G]TACTAAAAGCTTATTAACTTAATTT (SEQ ID NO: 97) | homozygous |
| NC_044379.1 | 49269535 | TGTTGATCAATTTTCCAGAATATT[G\|A]ATTACTTTTCATCACCCCTTATAAT (SEQ ID NO: 98) | heterozygous |
| NC_044379.1 | 51931932 | GCATTCAGGTCATTCACACTAATG[A\|T]TGGTCTATTCTTATCTCAGCAAAAA (SEQ ID NO: 99) | heterozygous |
| NC_044379.1 | 58878773 | TTCTAGCATAGACAGAAGTATAAT[G\|C]CTTGACATGTTTTTAAATGAAAACT (SEQ ID NO: 100) | heterozygous |
| NC_044379.1 | 62940605 | AGCATCATTGATGTTCTTTAGCAT[T\|A]TTTTTAGGGCACATTATTTTTTTTG (SEQ ID NO: 101) | heterozygous |

THE CLONING PROCESS FOR VEGETATIVE OR ASEXUAL REPRODUCTION

Asexual or vegetative propagation methods (also known as cloning) are well-known to those skilled in the art. 'Pure Red 3' is cloned according to the following method: Coco peat plugs are soaked in pH-adjusted water and kept warm. Cuttings measuring 10-12 cm are taken 3 nodes from the branch distal meristem and trimmed of lower leaves. The cuttings are dipped in water and a commercial rooting agent and inserted into the warmed plugs. Trays are kept in continuous light conditions and high humidity for 7 to 15 days until rooted. Rooted plants may be transferred directly into the field for outdoor growth or used for greenhouse growth.

It was observed that all the desired characteristics of each clone are transferred by vegetative reproduction in a consistent and uniform fashion. The characteristics of 'Pure Red 3' are stable and the variety remains true-to-type through multiple generations of vegetative reproduction.

GROWTH OF PLANTS IN INDOOR ENVIRONMENTS

Rooted clones are transferred to two-gallon pots containing growth medium consisting of a mixture of soil, peat and pearlite in a ratio of 3:3:1. Plants are grown in an indoor growth hall under completely supplied artificial high-pressure sodium (HPS) lighting (E-Papillon, 1000W, 400V). The air in the room was circulated with a fan and the humidity was kept constant at 45-55%. Commercial fertilizer is applied at a dose of 70-80% of the amount recommended by the manufacturer (Plagron, NL). The plants are grown for 10 days with a light intensity between 700-800 μmol m-2 s-1, 18 h light/6 h dark day-night photoperiod with a 24-25° C. day/18° C. night temperature. The photoperiod is then changed to a 12 h light /12 h dark day-night cycle and the light intensity increased by 100 μmol m-2 $s^{-1}$ per day for 7 days, at 25° C. day/23° C. night temperatures. During the following 60 days the light intensity is adjusted to 1400-1500 μmol $m^{-2}$ $s^{-1}$ with a 12 h light/12 h dark day-night photoperiod and a 24-25° C. day/18° C. night temperature. After a total of 84-91 days of growth after cloning, the flowers are harvested.

GROWTH OF PLANTS OUTDOORS

Field growth of 'Pure Red 3' was performed in Niederwil, CH (47°22'49.9"N 8°18'12.6"E) during the summer of 2022. The weather during the year of 2022 is presented in FIG. 11. Rooted clones were planted in the field on the 21$^{st}$ of July 2022 with a row distance of 1.5 m and planting distance of 750 cm. Plants were planted in foil strips for weed control and drip irrigation was installed under the foilips. Initial fertilizer was applied with a slurry and irrigation supplied as needed. Mature flowers were then collected during the first two weeks of October 2022.

DESCRIPTION OF THE NEW VARIETY

Figure 1:
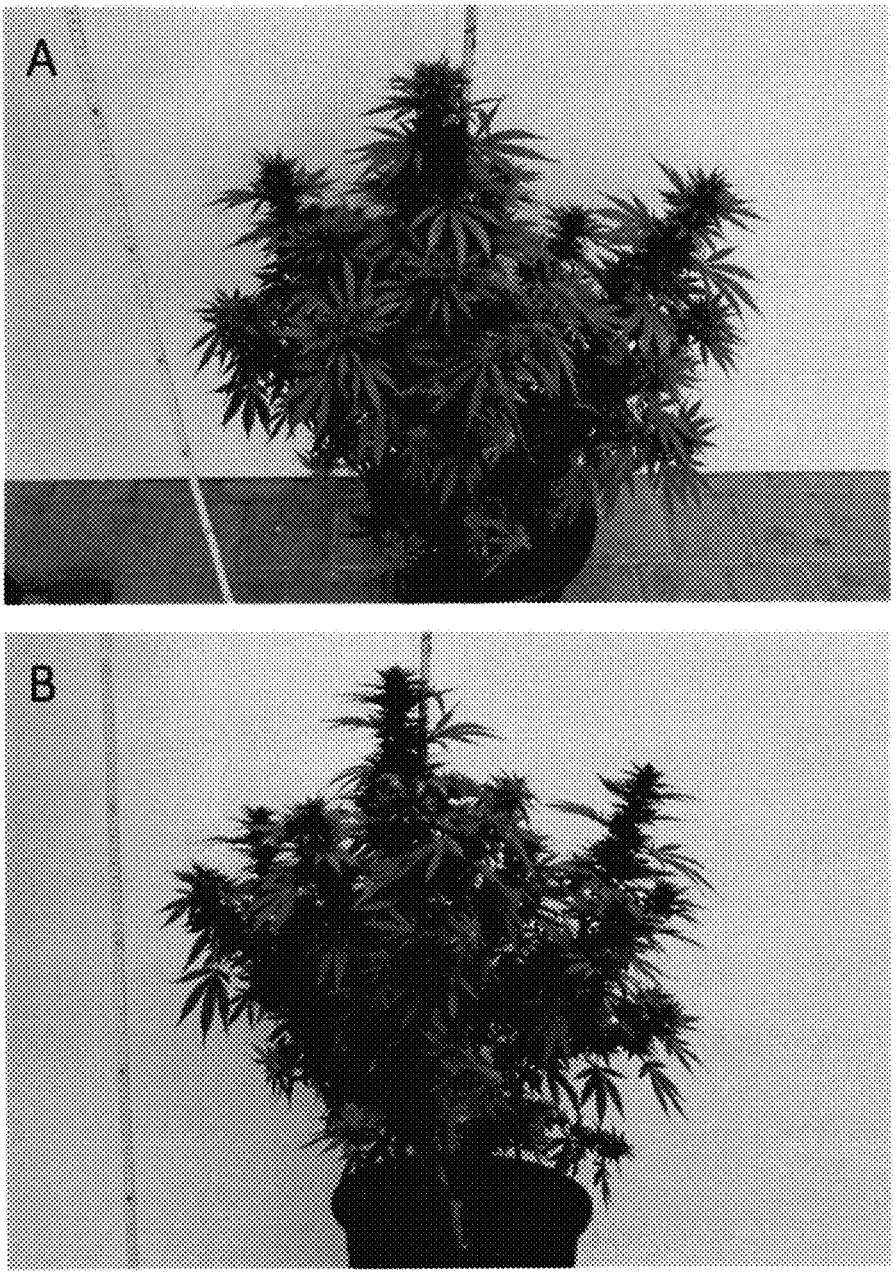
FIG. 1: Mature plants of the 'Pure Red 3' variety grown in greenhouse conditions. Photos taken from two different angles clearly illustrate the architecture of the plant. Ruler for scale with cm markings.
Figure 2:
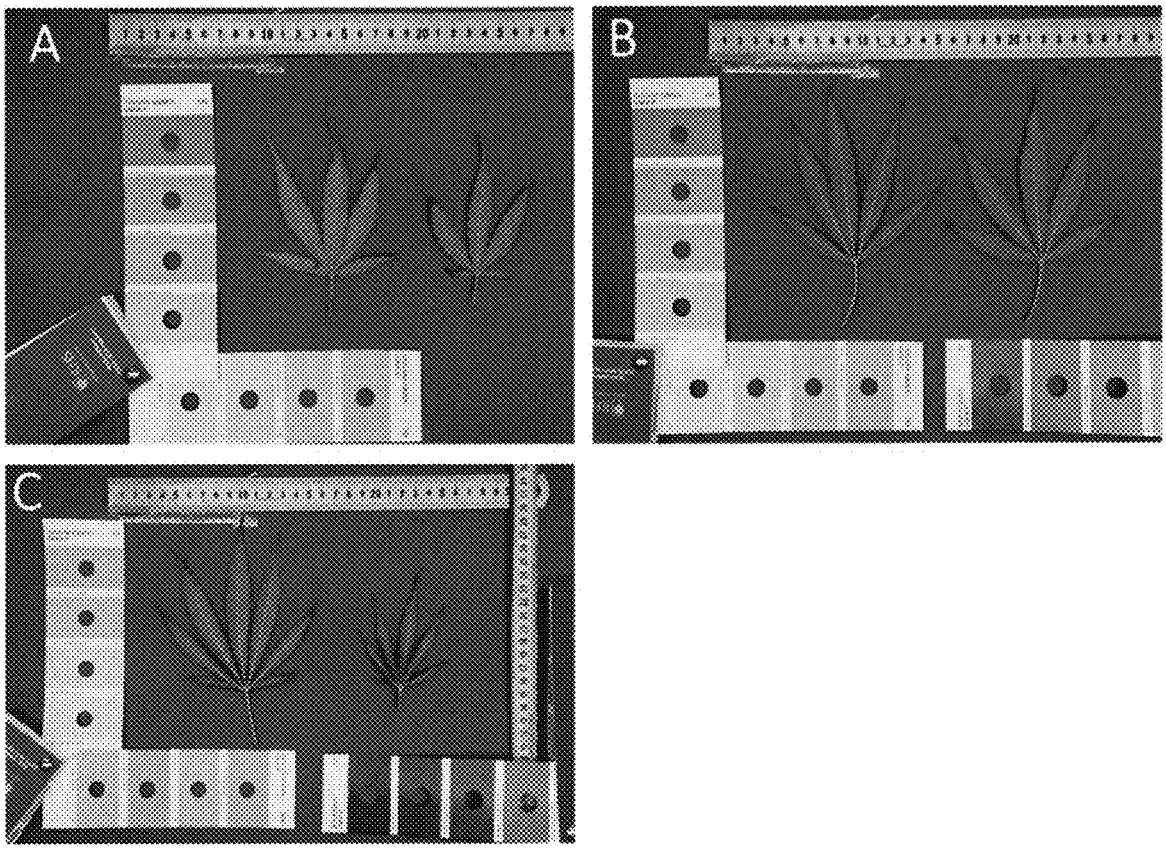
FIG. 2: Abaxial leaf surfaces sampled from the (A) lower, (B) middle, and (C) upper third of the mature 'Pure Red 3' plant. Ruler for scale with cm markings and RHS colors swatches alongside to indicate the color.
Figure 3:
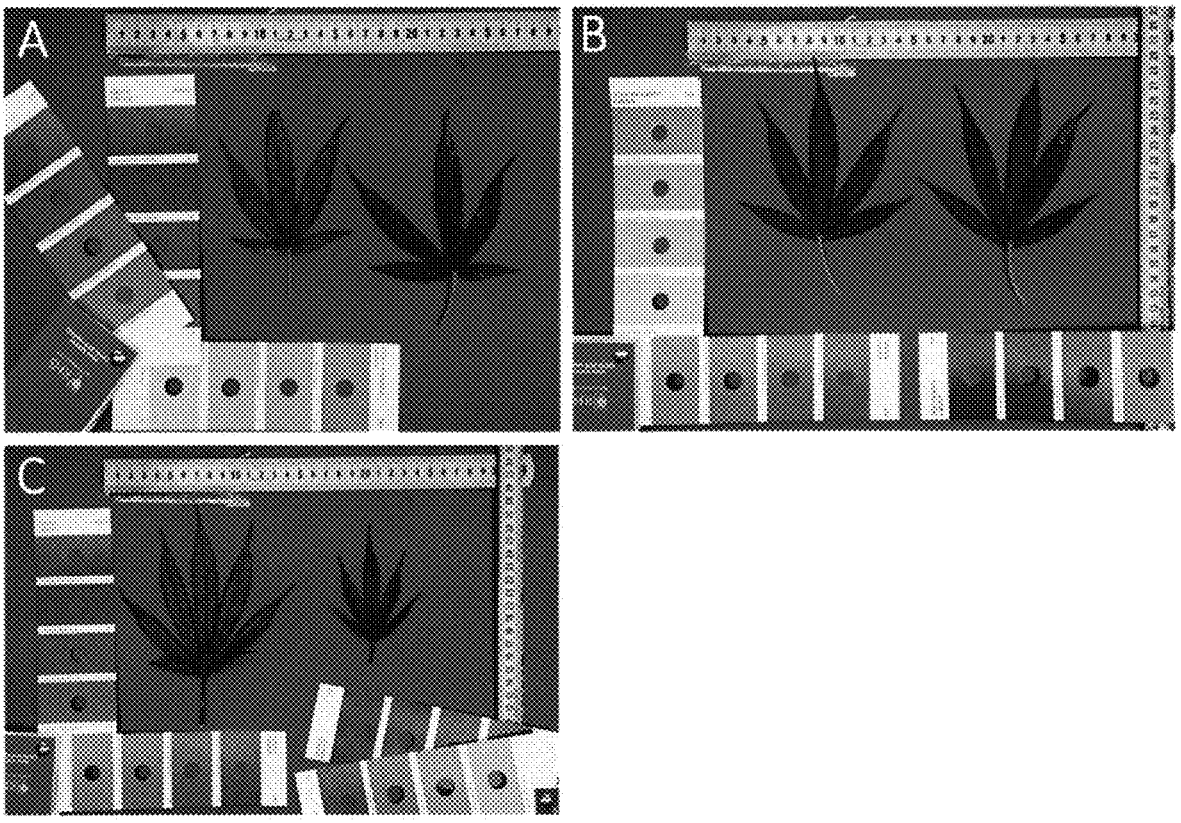
FIG. 3: Adaxial leaf surfaces sampled from the (A) lower, (B) middle, and (C) upper third of the mature 'Pure Red 3' plant. Ruler for scale with cm markings and RHS colors swatches alongside to indicate the color.
Figure 4:
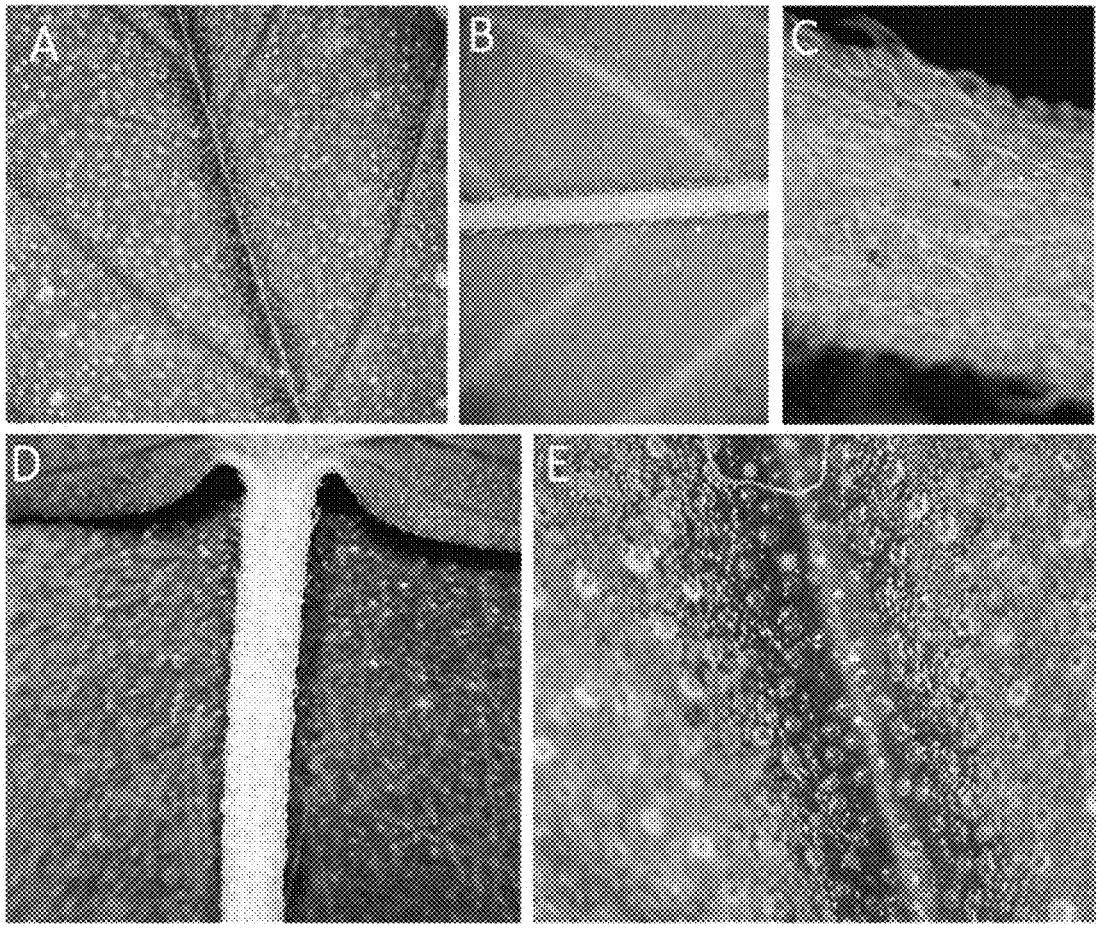
FIG. 4: Detailed photos of leaves from the lower third of the mature 'Pure Red 3' plants. (A) The adaxial leaf surface, (B) abaxial midrib, (C, D) adaxial petiole, (E) glandular bulbous trichomes on adaxial leaf surface.
Figure 5:
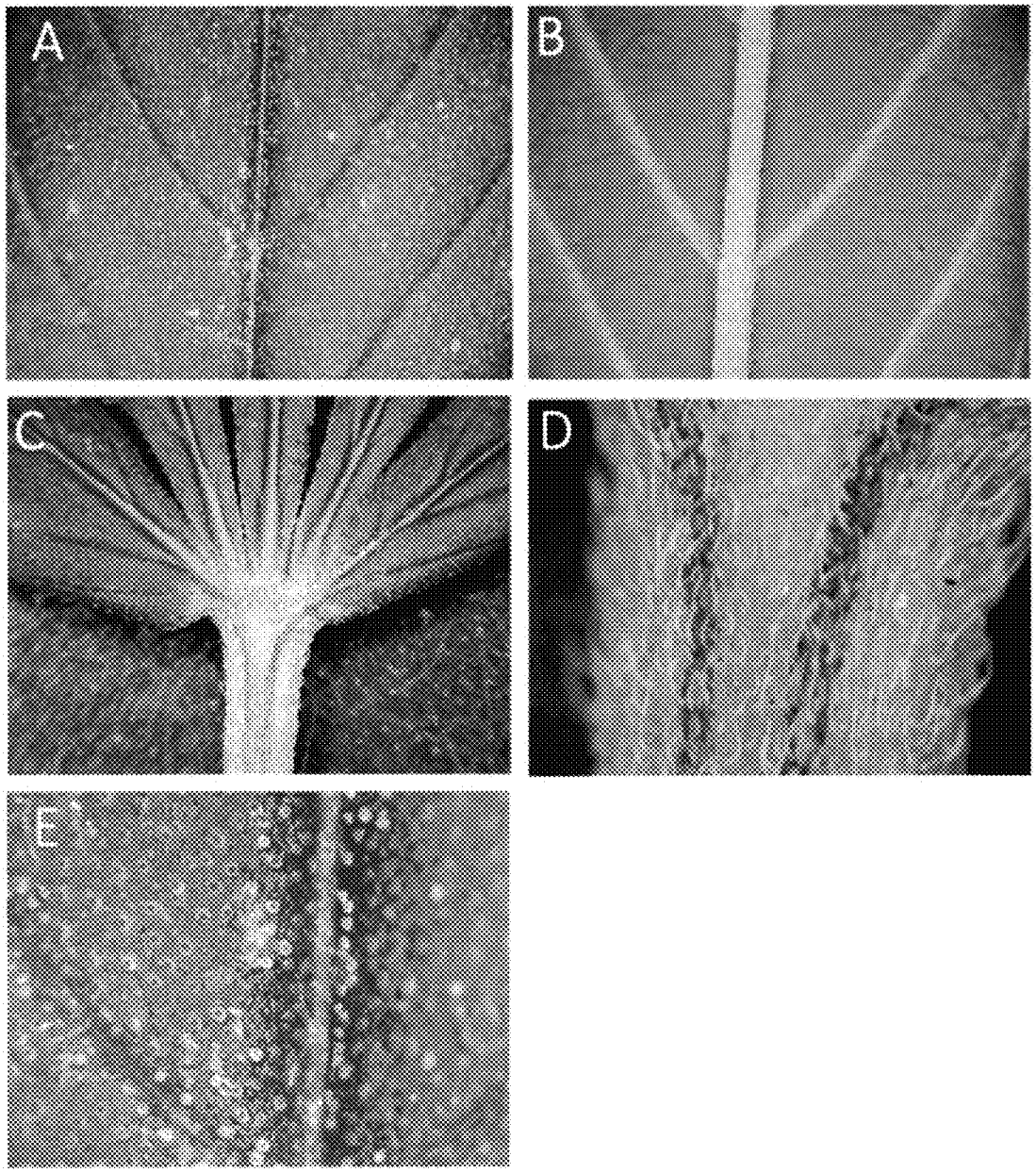
FIG. 5: Detailed leaf images from the middle third of the mature plant. (A) Adaxial midrib, (B) Abaxial midrib, (C, D) adaxial petiole with uni-cellular non-glandular hairs and purple anthocyanin coloration, (E) glandular bulbous trichomes on adaxial leaf surface.
Figure 6:
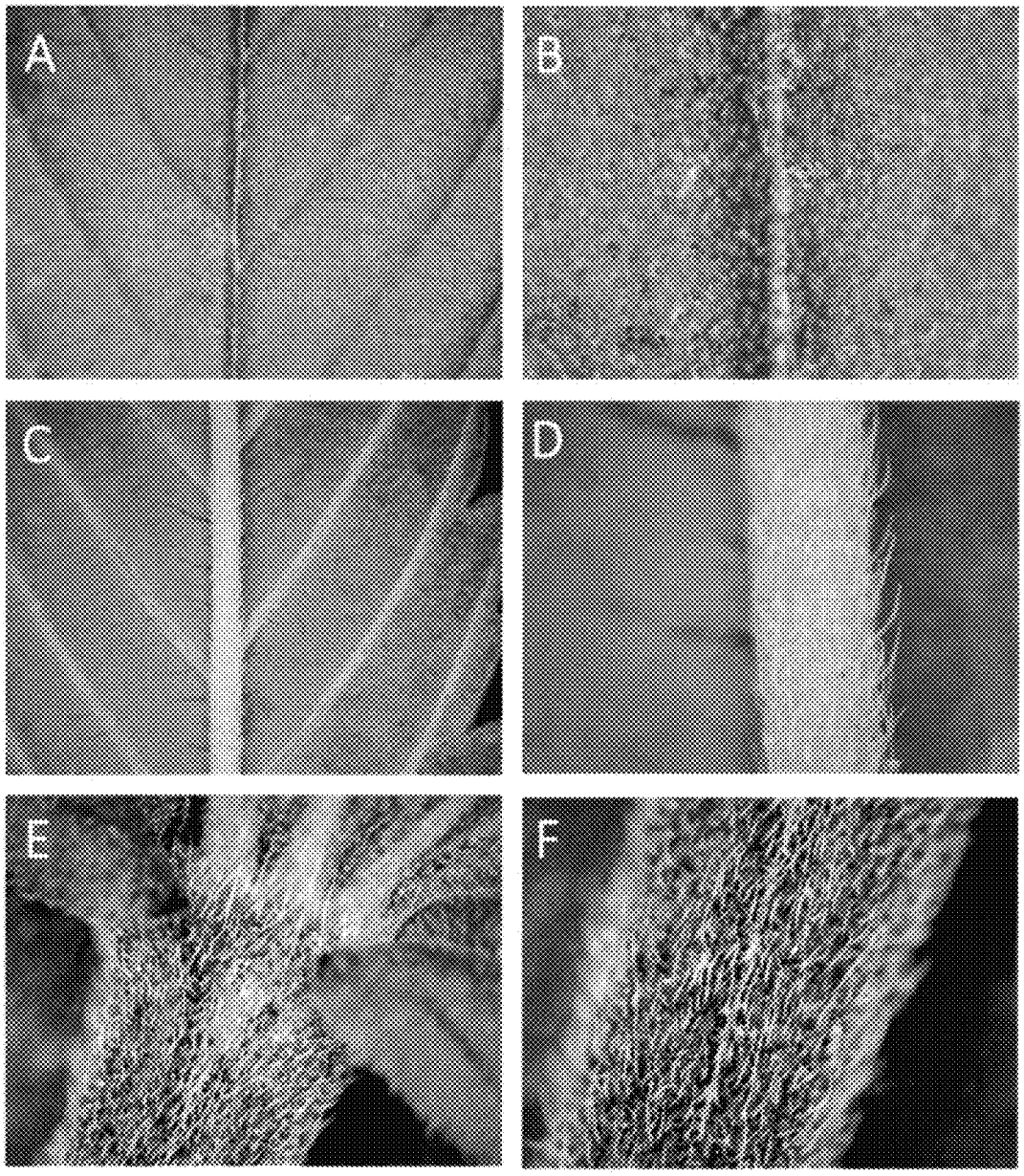
FIG. 6: Detailed leaf images from the upper third of the mature plant. (A, B) Adaxial leaf surface illustrating the presence of bulbous glandular trichomes, (C, D) abaxial leaf surface covered in uni-cellular non-glandular hair, (E, F) adaxial petiole showing significant purple anthocyanin coloration and uni-cellular non-glandular hairs.
Figure 7:
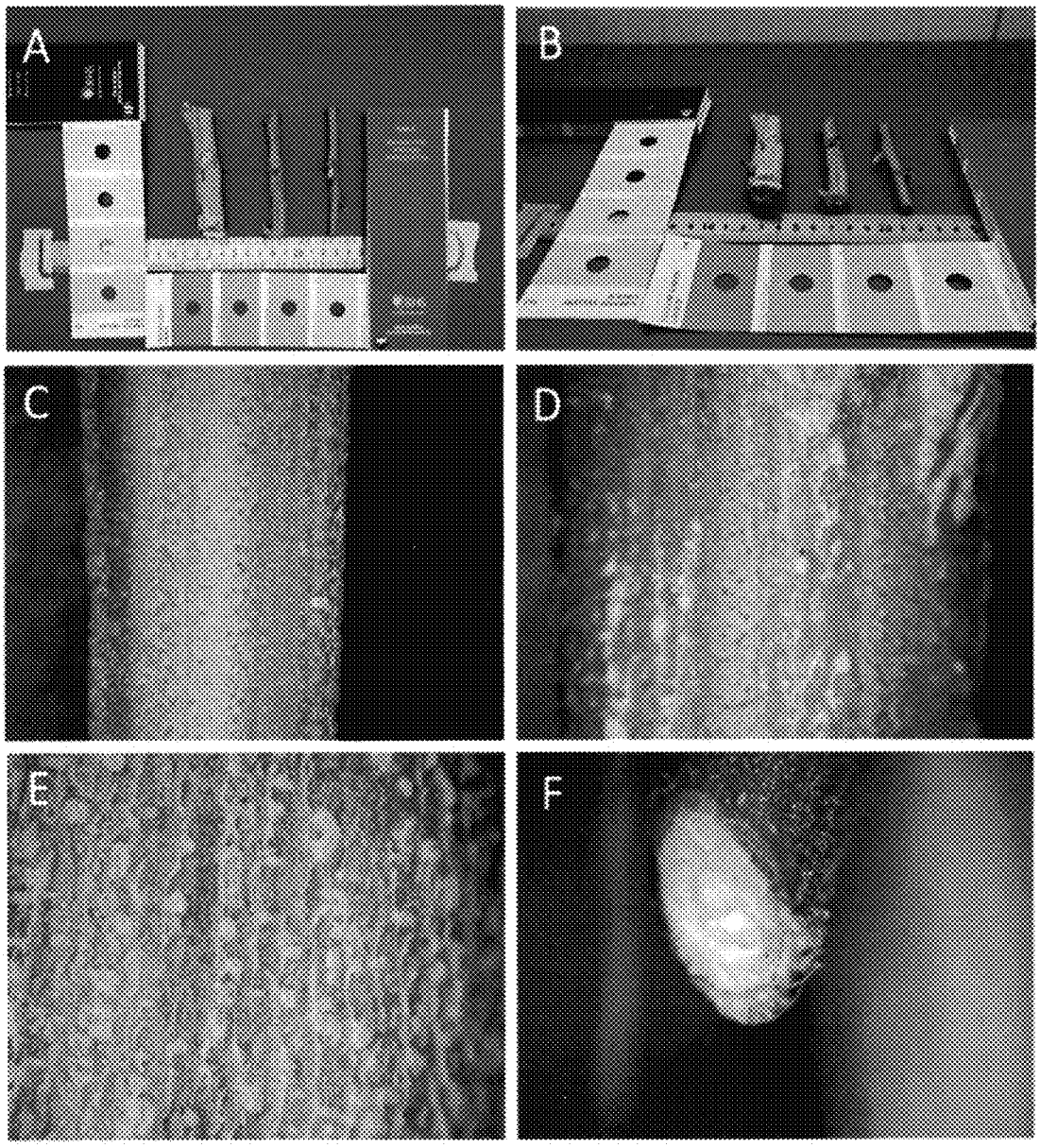
FIG. 7: 'Pure Red 3' stems. (A, B) Stem samples from the lower, middle and upper third of the plant are placed alongside a ruler for scale with cm markings and RHS colors swatches alongside to indicate the color. (C, D, E) Detailed photos of the stem surface illustrating the smooth stem with a solid, pithy center (F).
Figure 8:
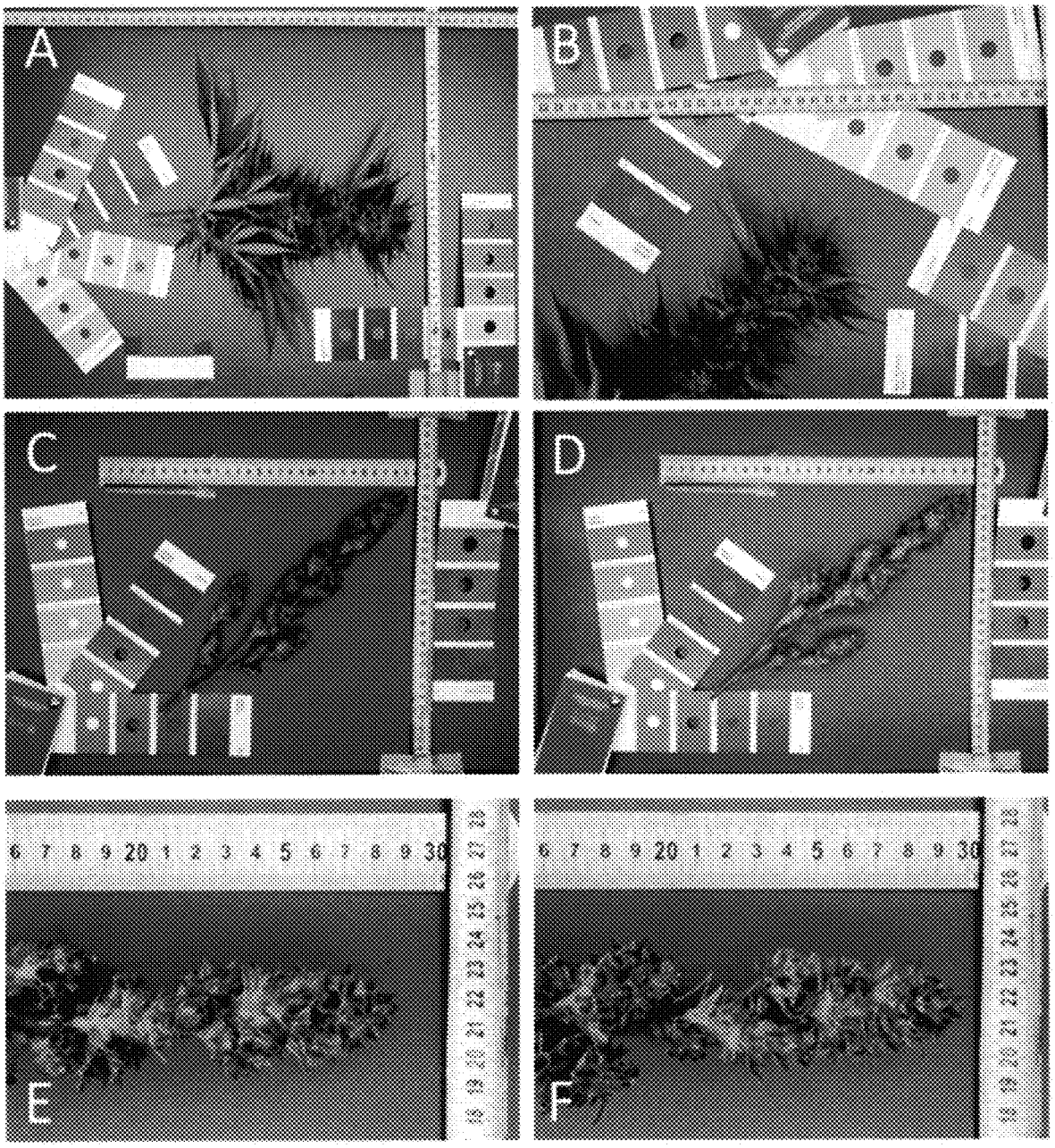
FIG. 8: Mature flowers from 'Pure Red 3' plants grown in a greenhouse. (A, B) Untrimmed flowers and (C-F) hand trimmed flowers. Ruler for scale with cm markings and RHS colors swatches alongside to indicate the color.
Figure 9:
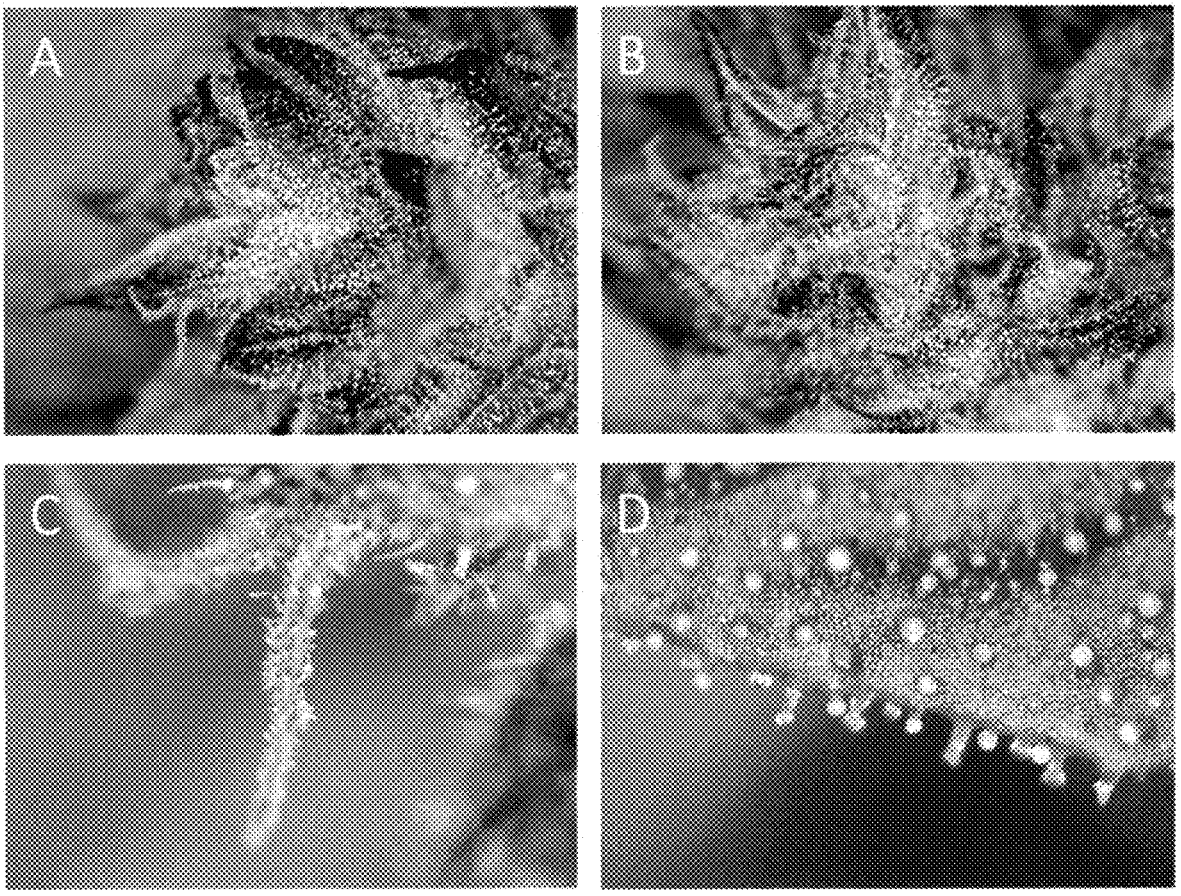
FIG. 9: Detailed images of 'Pure Red 3' flowers. (A, B) Floral bracts with distinct purple anthocyanin coloration, (C) orange/grey stigmas protruding from the floral bracts, (D) capitate stalked trichomes on a reduced leaf that emerge from between the inflorescences.
Figure 10:
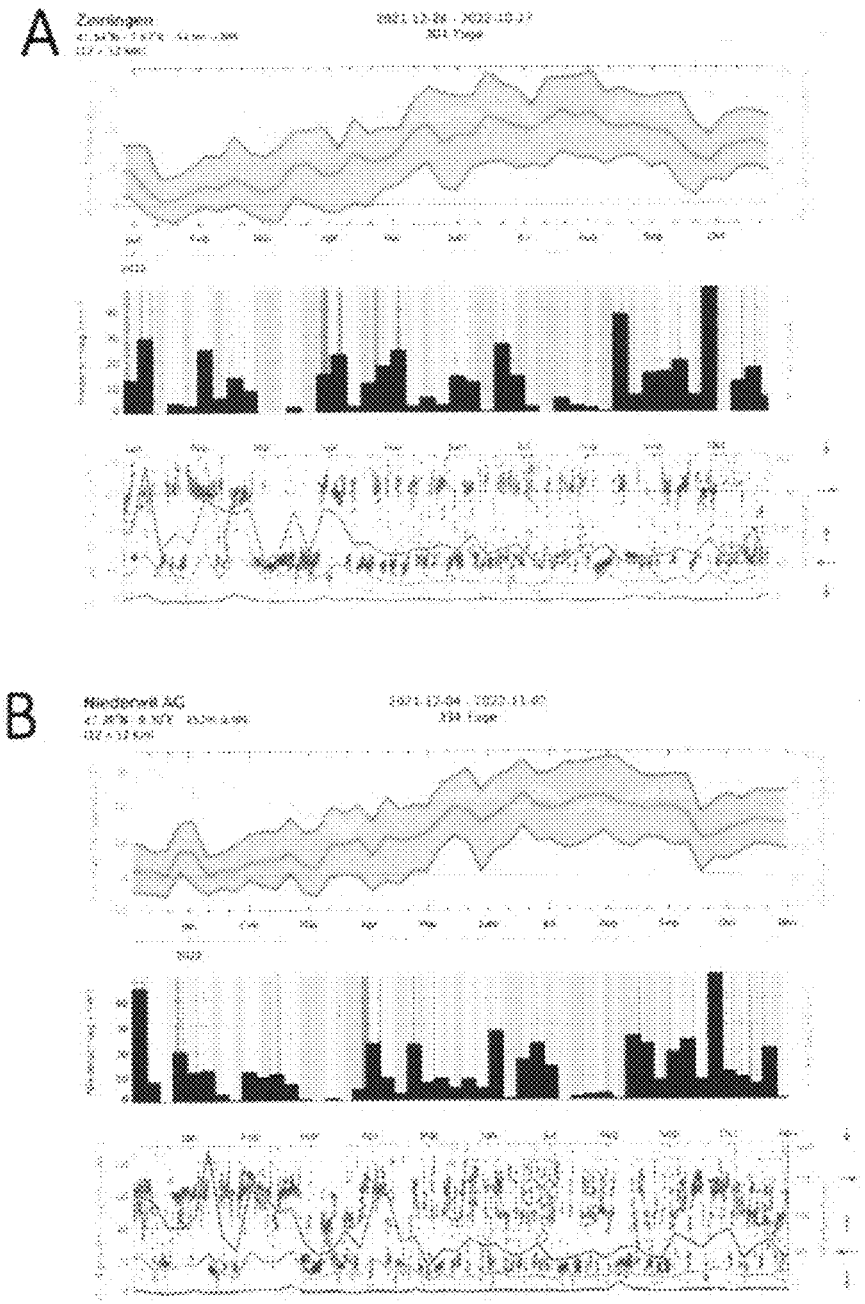
FIG. 10: Annual temperature, rainfall, and wind data for (A) Zeiningen and (B) Niederwil for 2022.
Figure 11:
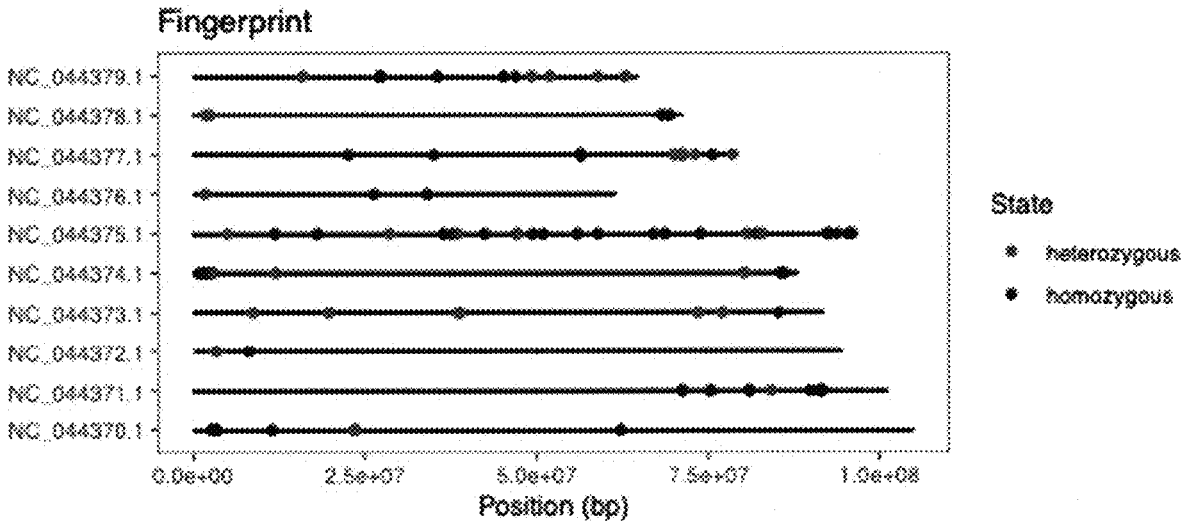
FIG. 11: A graphical representation of the single nucleotide polymorphisms (SNP) and haplotypes (HAPs) contained within the genome of 'Pure Red 3' when compared to the publicly available reference genome of cs10 (Assembly: GCF_900626175.1).

The 'Pure Red 3' plants described herein were grown both in nurseries, climate-controlled growth facilities in Zeiningen, CH, 4314 (47°32'53.5"N 7°51'53.2"E), and in the field in Niederwil, CH (47°22'49.9"N 8°18'12.6"E). Observed phenotypes may vary in different environmental conditions.

Plants used for the botanical description are annual, herbaceous, upright, tap-rooted plants. They are *Cannabis* hybrid species and the particular variety described herein is designated 'Pure Red 3'.

Throughout this specification, color names signify that the name of that color, as used in common speech is aptly descriptive. Color number descriptions were obtained using the 6$^{th}$ revised edition of the RHS (Royal Horticultural Society) color chart.

'Pure Red 3' is a cross between multiple plants of the pollen donor variety 'Amnesia Haze' (unpatented) and several plants of the pollen acceptor variety 'Strawberry Haze' (unpatented). The initial cross was made in 2018 in Zeiningen, Switzerland. The resulting F1 seeds were grown, cloned, and the clones used for crossing i.e. selfed. The F2 seeds were grown, and from this population 'Pure Red 3' was selected. The selection criteria were based on the following characteristics: Pungent strawberry smell in the mature flower, flower density, and a highly branched plant structure. The variety was first vegetatively reproduced on the 12$^{th}$ of April 2019 and the resultant plants screened for strong strawberry aroma and selected based on production relevant phenotypes. The progeny with the most stable desirable chemotype was assigned the name, 'Pure Red 3'. 'Pure Red 3' continues to be vegetatively reproduced by cloning in Zeiningen, Switzerland.

Compared to 'Strawberry Haze', 'Pure Red 3' has a much lower total CBD content (12.69% vs 21%), and higher THC content (0.57% vs <0.2%). 'Pure Red 3' also has a distinct and notably stronger strawberry aroma. 'Pure Red 3' has CBD concentrations comparable to those in 'Amnesia Haze'. The strong strawberry aroma of 'Pure Red 3' does not resemble the lemon and floral notes found in 'Amnesia Haze'. 'Pure Red 3' notably has distinct purple anthocyanin coloration in the apical regions that are not evident in the parent varieties.

The new variety 'Pure Red 3' is a *Cannabis* strain that is distinct from the commercial variety 'Bubblegura' (unpatented). The new variety 'Pure Red 3' has a lower total CBD content (12.69% vs. 15%) and a similar THC content (0.57% vs. 0.6%) as 'Bubblegum'. However, the new variety 'Pure Red 3' has a strong strawberry aroma, while 'Bubblegum' has a sweet and mild-citrus aroma. Additionally, the new variety 'Pure Red 3' displays a distinct purple anthocyanin coloration in the apical regions, while 'Bubblegum' does not.

The new variety 'Pure Red 3' is also distinct from the variety 'Cannatonic' (unpatented). The new variety 'Pure Red 3' has a lower CBD content (12.69% vs. 17.5%) than 'Cannatonie', but a similar THC content (0.57% vs. 0.6%). Additionally, the new variety 'Pure Red 3' has a strong strawberry aroma compared to the woody and clove aromas of 'Cannatonic'. Lastly, unlike the new variety 'Pure Red 3', 'Cannatonic' does not display a distinct purple anthocyanin coloration in the apical regions.

Below is a detailed description of the new variety 'Pure Red 3'. Unless otherwise stated measurements were taken from mature plants grown in a greenhouse. The 'Pure Red 3' cultivar is a mixed hybrid of the *Cannabis* sp. It is naturally obtained and not the result of any genetic modification techniques.

Plant:

*Plant life form and growth habit.*—An annual herbaceous plant described as broad, upright, tap-rooted.

*Plant propagation.*—Asexually propagated by cutting and cloning methods.

*Propagation ease.*—'Pure Red 3' is easy to propagate.

*Height.*—Approximately 40 cm-70 cm.

*Width.*—Approximately 20 cm to 40 cm.

*Plant vigor.*—Medium — 'Pure Red 3' bears mature flowers with a high flower:total biomass without the requirement for excessive growth.

*Time to harvest.*—From time of planting the plant will take approximately 9.7 weeks to be harvest-ready.

*Resistance to pathogens.*—Moderate to high susceptibility to *Botrytis cinerea* with the tipping point after maturity and at high humidity. 'Pure Red 3' has low to moderate susceptibility to powdery mildew and leaf spot in outdoor conditions. In greenhouse environments it is highly susceptible to powdery mildew. 'Pure Red 3' shows high resistance to insect pests.

*Genetic modification.*—It is naturally obtained and not the result of any genetic modification techniques.

*Conditions of flowering.*—'Pure Red 3' flowers once the daylight period is reduced to 14.3 hours daylight.

*Hardiness.*—'Pure Red 3' easily tolerates temperatures up to 32° C.

*Breaking action.*—'Pure Red 3' is short and sturdy and highly resistant to breaking during heavy winds. This plant is not prone to lodging.

*Rooting behavior.*—When propagated according to Puregene's standard operating procedures, it roots vigorously.

Leaf:

*Arrangement.*—Alternating.

*Shape.*—Palmately compound.

*Structure.*—Leaflet blades are very elongated, elliptical, lanceolate with acute to accuminate tips and bases.

*Margins.*—Serrated with teeth forward pointing.

*Hairs.*—Extremely fine sericreous hairs pointing toward the leaf tips.

*Mature leaf measurements.*—Leaf length with petiole: Approximately 9-15 cm. Petiole length: Approximately 2.5-4 cm. Stipule length and shape: Approximately 0.2 cm to 0.8 cm linear with acute tip. Leaflet number: About 5. Middle leaflet length:width: Approximately 9:1.5. Teeth on middle leaflet: Approximately 18 to 28. Middle largest leaflet length: Approximately 9 cm. Width of central leaflets: Approximately 1.5 cm.

*Leaflet apex shape.*—Acuminate acute.

*Adaxial leaf trichomes.*—Capitate stalked, capitate sessile and cystolithic trichomes.

*Abaxial leaf trichomes.*—Capitate stalked, capitate sessile and cystolithic trichomes.

*Abaxial petiole color range.*—About Medium Yellow-Green 144B with gradual anthocyanin coloration of Medium Red-Purple 58A during flowering.

*Adaxial petiole color range.*—About Medium Yellow-Green 144B with gradual anthocyanin coloration of Medium Red-Purple 58A and 58B during flowering.

*Stipule color range.*—About Dark Green 137A and 137B.

*Leaflet color of the adaxial surface.*—About Dark Green 137A and 137B in the lower leaves to Dark Green 137B in the middle leaves and becoming slightly mottled with purple Dark Purple 79A toward the apical growth point.

*Leaflet color of the abaxial surface.*—Ranging from Medium Yellow-Green 144A in the lower leaves to Medium Yellow-Green 144B in the middle of the plant with distal leaf tips transitioning to Medium Red-Purple 58A. Leaves proximal to the flowers are yellow green Light Yellow-Green 144C mottled with red purple coloration of Dark Red-Purple 59A.

*Leaflet glossiness.*—Average, becoming more matt at the apical ends as flowers mature.

*Midrib shape.*—Prominent and continuous throughout each leaflet.

*Midrib color.*—The midrib on the adaxial leaf surface appears around Dark Green 137A. On the abaxial side it appears about Light Yellow-Green 145D.

*Aroma.*—'Pure Red 3' has a strong and distinct strawberry fruit aroma on the living plant which remains pungent and distinctive post freeze drying and through production.

Stem:

*Shape.*—The stem is smooth with a solid center.

*Diameter.*—Approximately 1.5 cm-2.5 cm.

*Color.*—Ranging from Light Yellow-Green 144D at the base to Medium Yellow-Green 144A near the apical flower.

*Main stem groove.*—Very shallow longitudinal ridge in stem proximal to flowering end, which quickly smooths at the middle third and lower third of the stem. The lower third is woody with a solid pith throughout.

*Stem trichomes.*—Capitate sessile glandular trichomes and unicellular non-glandular trichomes found in middle and upper portions of the stem.

*Stem internode length.*—Short during early vegetative phases elongating as the plant matures. During late vegetative phase the average length of the internodes is medium. The internodes shorten exponentially towards the flowering ends exhibiting as very short directly below the compound inflorescence.

Inflorescence:

*Flowering habit.*—Elongated compound spikes/panicles approximately 5 cm to 10 cm in length. During vegetative phase individual flowers occur at nodes along the stem and branches. Upon flower initiation flowers appear as clusters, or compound inflorescences, as a result of higher order branching and shortened internodes. Terminal inflorescences appear as compressed and dense while more distal inflorescences gradually decrease in size and density with a scattered appearance.

*Proportion of female flowers.*—100%.

*Inflorescence position.*—Above.

*Flower arrangement.*—Touching intermediate. Individual flowers (bracteoles) on each mature, compound inflorescences are tightly packed, congested, concentrated and crowded, touching and overlapping with stigmas curling over adjacent bracteoles with maturity.

*Number of floral bracts.*—100s to 1000s of individual floral bracts per plant. About 20-40 compound inflorescences per plant.

*Individual flower shape.*—Each individual flower has one ovary enclosed in an urceolate bract with two long filiform stigmas protruding from each ovary and exiting above the bract.

*Compound inflorescence shape.*—Compound inflorescences are ovaloid in shape with bilateral symmetry.

*Flower compound inflorescence diameter.*—The average diameter around the trimmed terminal flower compound is 3.5 cm.

*Pistil length.*—The length from the base of the ovary to the tips of the stigmas is approximately 2 mm to 6 mm.

*Style length.*—There is no discernible style connecting the stigmas to the ovary. The stigma refers to the entire length from the upper curve of the ovary to the tip of the stigmas.

*Bract shape and color.*—Urceolate with a bright green base Medium Yellow-Green 144A to Dark Green 137A and 137B with bright purple tip about Dark Red-Purple 59A.

*Bract length.*—Approximately 2 mm.

*Bract width.*—Approximately 2 mm to 6 mm.

*Bract texture.*—Bract is covered in capitate staked, capitate sessile and bulbous resinous trichomes.

*Bract base.*—Bulbous.

*Bract apex.*—Acuminate acute.

*Stigma shape.*—Extremely elongated, elliptical, filiform and visible as hair-like filaments on the surface of flower compounds.

*Stigma length (from the upper surface of the ovary to the tip of the stigma).*—Approximately 2 mm to 6 mm.

*Stigma color.*—The color changes from a white color during early flowering to Medium Greyed-Orange 167A, Medium Greyed-Orange 163A and Light Greyed-Orange 163B turning darker to Dark Greyed-Orange 166B after 4 days of drying the flower.

*Trichome color.*—Initially clear becoming cloudy/milky white and then developing an amber color at 5 weeks post flowering.

*Trichome shape.*—Capitate stalked and/or capitate sessile and/or bulbous. All flowering parts including the bracteoles and bracts are covered in capitate stalked, capitate sessile and bulbous glandular trichomes.

*Terminal bud shape.*—Acute ovoid.

*Terminal bud color.*—At maturity the terminal bud appears about Dark Green 137A with Dark Purple 79A accents partially covered by Medium Greyed-Orange 167A, Medium Greyed-Orange 163A and Light Greyed-Orange 163B hair-like stigmas.

*Male flower characteristics.*—'Pure Red 3' clones are propagated only as females and the male flower characteristics are not relevant to the physical botanical characterization of this variety.

*Cannabinoid contents.*—$CBD_{max}$-12.69%, $THC_{max}$-0.57%, $CBG_{max}$-0.17%, $CBC_{max}$-0.72%, $CBDV_{max}$-0.70%.

*Flower fragrance.*—Pungent strawberry fruit aroma.

*Flower shipping quality.*—It is a dense appealing flower when trimmed, cured and packaged according to quality guidelines. Dry flowers are of high quality and suitable as a direct-to-consumer commodity.

*Flower storage life.*—A minimum of 1 year if packaged according to quality guidelines.

*Flower productivity.*—Approximately 75-100 g of dried flower biomass per plant grown outdoors.

*Flowering season.*—Flowering is initiated around 10 August when the daylight reduces to 14.30 h. This may change at different latitudes. From day of flowering, the plant takes approximately 6.8 weeks to reach maturity.

SEQUENCE LISTING

```
Sequence total quantity: 101
SEQ ID NO: 1            moltype = DNA  length = 50
FEATURE                 Location/Qualifiers
misc_difference         25
                        note = g or a
```

-continued

```
source                  1..50
                        mol_type = genomic DNA
                        organism = Cannabis sativa
SEQUENCE: 1
ttatcgtttt tttggttttt gatanatcac acaaatcatt gtatttatcc            50

SEQ ID NO: 2            moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 2
taaaaataga aagaaagacc attcnaagaa taattttttt ttatgcattt            50

SEQ ID NO: 3            moltype = DNA  length = 50
FEATURE                 Location/Qualifiers
misc_difference         25
                        note = t or c
source                  1..50
                        mol_type = genomic DNA
                        organism = Cannabis sativa
SEQUENCE: 3
aggctttaag gtaatactaa tacangaggc ataaatataa aactgacagc            50

SEQ ID NO: 4            moltype = DNA  length = 50
FEATURE                 Location/Qualifiers
misc_difference         25
                        note = t or a
source                  1..50
                        mol_type = genomic DNA
                        organism = Cannabis sativa
SEQUENCE: 4
tgttggatca tgagctgaat ttctnatttc attagcagaa ggaaacatag            50

SEQ ID NO: 5            moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 5
tctcactttt tcccacaata ccacnagagt ttccagatga ggttccacca            50

SEQ ID NO: 6            moltype = DNA  length = 50
FEATURE                 Location/Qualifiers
misc_difference         25
                        note = c or g
source                  1..50
                        mol_type = genomic DNA
                        organism = Cannabis sativa
SEQUENCE: 6
aaacaattgc aactctcaca atttnagcgt tcagatttgg caccaaaatt            50

SEQ ID NO: 7            moltype = DNA  length = 50
FEATURE                 Location/Qualifiers
misc_difference         25
                        note = a or c
source                  1..50
                        mol_type = genomic DNA
                        organism = Cannabis sativa
SEQUENCE: 7
aataattatt aaaaattaac tttcntaaac caaataccaa aatatttaaa            50

SEQ ID NO: 8            moltype = DNA  length = 50
FEATURE                 Location/Qualifiers
misc_difference         25
                        note = g or a
source                  1..50
                        mol_type = genomic DNA
                        organism = Cannabis sativa
SEQUENCE: 8
aaattttact tttaggtata cacantagtt attcaattgg tatttaacga            50
```

-continued

```
SEQ ID NO: 9            moltype = DNA  length = 50
FEATURE                 Location/Qualifiers
misc_difference         25
                        note = g or c
source                  1..50
                        mol_type = genomic DNA
                        organism = Cannabis sativa
SEQUENCE: 9
tacctagttc ggaaggctgt cttcnggata tcctcttctc gaattctcaa            50

SEQ ID NO: 10           moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 10
agatagatct cccacacata tatanagtat ttttgtttta gttttcactt            50

SEQ ID NO: 11           moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 11
tttgttgtgc aaagaataca ttttntaagt ttaaggccac accatcatgt            50

SEQ ID NO: 12           moltype = DNA  length = 50
FEATURE                 Location/Qualifiers
misc_difference         25
                        note = g or a
source                  1..50
                        mol_type = genomic DNA
                        organism = Cannabis sativa
SEQUENCE: 12
ctctaaaaac ttcctctgga tatantcctt tgaccgaact tgttaaagaa            50

SEQ ID NO: 13           moltype = DNA  length = 50
FEATURE                 Location/Qualifiers
misc_difference         25
                        note = a or g
source                  1..50
                        mol_type = genomic DNA
                        organism = Cannabis sativa
SEQUENCE: 13
cagtagcaat gtaataggag aaatncaaag aaacaccttg agctcaaaaa            50

SEQ ID NO: 14           moltype = DNA  length = 50
FEATURE                 Location/Qualifiers
misc_difference         25
                        note = a or c
source                  1..50
                        mol_type = genomic DNA
                        organism = Cannabis sativa
SEQUENCE: 14
tgtgtagcaa atgctttaat attgncatcc gattgggtta ctgattcgat            50

SEQ ID NO: 15           moltype = DNA  length = 50
FEATURE                 Location/Qualifiers
misc_difference         25
                        note = t or c
source                  1..50
                        mol_type = genomic DNA
                        organism = Cannabis sativa
SEQUENCE: 15
ccatctcagg aaattggaag attcntcaaa caacctgtat taattgttcc            50

SEQ ID NO: 16           moltype = DNA  length = 50
FEATURE                 Location/Qualifiers
misc_difference         25
                        note = c or a
source                  1..50
                        mol_type = genomic DNA
                        organism = Cannabis sativa
```

-continued

```
SEQUENCE: 16
cgaaaaacta aaaacatccc aattnaaata tcaacaacag taattctaat            50

SEQ ID NO: 17          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 17
gtactttcaa tactgcctcc aagangccaa ataagtattt gagtttttt            50

SEQ ID NO: 18          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 18
tctttattgg tttgtcacac ttgtngttcg gtggaatccc gtatatcgtc            50

SEQ ID NO: 19          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 19
ttgtaattga aaacaattag aaacntaacc ttggagccta ttcaggcata            50

SEQ ID NO: 20          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 20
gaatttagag atgttattgg atccnctgct ttctgttgaa ccttttaact            50

SEQ ID NO: 21          moltype = DNA  length = 50
FEATURE                Location/Qualifiers
misc_difference        25
                       note = g or c
source                 1..50
                       mol_type = genomic DNA
                       organism = Cannabis sativa
SEQUENCE: 21
ccatggcgct ggcgtttgtc atgantactg tcttgtggct cttcatgcct            50

SEQ ID NO: 22          moltype = DNA  length = 50
FEATURE                Location/Qualifiers
misc_difference        25
                       note = t or g
source                 1..50
                       mol_type = genomic DNA
                       organism = Cannabis sativa
SEQUENCE: 22
gtacctttt ctctgaatga aaatntgaaa tttacaatat aactcaataa            50

SEQ ID NO: 23          moltype = DNA  length = 50
FEATURE                Location/Qualifiers
misc_difference        25
                       note = c or a
source                 1..50
                       mol_type = genomic DNA
                       organism = Cannabis sativa
SEQUENCE: 23
accctatagt attatttact tatgncataa aaaagtaaat tataccctca            50

SEQ ID NO: 24          moltype = DNA  length = 50
FEATURE                Location/Qualifiers
misc_difference        25
                       note = a or g
```

-continued

```
source                  1..50
                        mol_type = genomic DNA
                        organism = Cannabis sativa
SEQUENCE: 24
gacttgtcaa taacataaat tcatntttgc attagatatt tgcatatatt            50

SEQ ID NO: 25           moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 25
aggttgatgc agattaatct ccaancttaa aaattggcag taatagtctc            50

SEQ ID NO: 26           moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 26
taacagtttt taaatgcatt aaccnaaaat agttagaatt catgtcaagt            50

SEQ ID NO: 27           moltype = DNA  length = 50
FEATURE                 Location/Qualifiers
misc_difference         25
                        note = t or c
source                  1..50
                        mol_type = genomic DNA
                        organism = Cannabis sativa
SEQUENCE: 27
tgacgccgga aaaattgtcg gagtngctgc caacgctgga aaattctgac            50

SEQ ID NO: 28           moltype = DNA  length = 50
FEATURE                 Location/Qualifiers
misc_difference         25
                        note = a or g
source                  1..50
                        mol_type = genomic DNA
                        organism = Cannabis sativa
SEQUENCE: 28
accagaagca aagaatagca tgtcntattc atatggatat attatttgaa            50

SEQ ID NO: 29           moltype = DNA  length = 50
FEATURE                 Location/Qualifiers
misc_difference         25
                        note = t or g
source                  1..50
                        mol_type = genomic DNA
                        organism = Cannabis sativa
SEQUENCE: 29
ggcaaatgtc taaatagttc tagcnaacca ataatacagt agtcaaacag            50

SEQ ID NO: 30           moltype = DNA  length = 50
FEATURE                 Location/Qualifiers
misc_difference         25
                        note = t or c
source                  1..50
                        mol_type = genomic DNA
                        organism = Cannabis sativa
SEQUENCE: 30
ctagctgcca ttggggttga tgganctaat tcaatctttc ccattgcata            50

SEQ ID NO: 31           moltype = DNA  length = 50
FEATURE                 Location/Qualifiers
misc_difference         25
                        note = a or t
source                  1..50
                        mol_type = genomic DNA
                        organism = Cannabis sativa
SEQUENCE: 31
tctcacagtt cccttaccaa aatanatata aggaaaagtg ttttgacatc            50
```

-continued

```
SEQ ID NO: 32          moltype = DNA  length = 50
FEATURE                Location/Qualifiers
misc_difference        25
                       note = c or g
source                 1..50
                       mol_type = genomic DNA
                       organism = Cannabis sativa
SEQUENCE: 32
ggtatatata taatactttt tctantcctt tatattcaca taattaacaa            50

SEQ ID NO: 33          moltype = DNA  length = 50
FEATURE                Location/Qualifiers
misc_difference        25
                       note = t or c
source                 1..50
                       mol_type = genomic DNA
                       organism = Cannabis sativa
SEQUENCE: 33
aaaaaaaaaa acagtataag atacntggtt acccttttatg gtaactggtt            50

SEQ ID NO: 34          moltype = DNA  length = 50
FEATURE                Location/Qualifiers
misc_difference        25
                       note = a or t
source                 1..50
                       mol_type = genomic DNA
                       organism = Cannabis sativa
SEQUENCE: 34
actcatgggt ttagaaaagg gatanttaca taagacatca tcttttgtaa            50

SEQ ID NO: 35          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 35
tctttttatt cgtttcggat ctagngtttt gcaaaagtta cagattaaac            50

SEQ ID NO: 36          moltype = DNA  length = 50
FEATURE                Location/Qualifiers
misc_difference        25
                       note = g or t
source                 1..50
                       mol_type = genomic DNA
                       organism = Cannabis sativa
SEQUENCE: 36
tgtgcggatt cctttatcta tcttntcgta attgaatagc agttacaata            50

SEQ ID NO: 37          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 37
gaaaaatcct ggtgttgttc tttgnaatct tgattttgtg tgtttgaatt            50

SEQ ID NO: 38          moltype = DNA  length = 50
FEATURE                Location/Qualifiers
misc_difference        25
                       note = a or c
source                 1..50
                       mol_type = genomic DNA
                       organism = Cannabis sativa
SEQUENCE: 38
tatcaaagct taaacggaat aatanggttt tagtaattga ataaataata            50

SEQ ID NO: 39          moltype = DNA  length = 50
FEATURE                Location/Qualifiers
misc_difference        25
                       note = c or a
source                 1..50
                       mol_type = genomic DNA
                       organism = Cannabis sativa
```

-continued

```
SEQUENCE: 39
gactcctccc ttttctcttg gaacnataga aataagaaat tggaacttag            50

SEQ ID NO: 40          moltype = DNA  length = 50
FEATURE                Location/Qualifiers
misc_difference        25
                       note = a or c
source                 1..50
                       mol_type = genomic DNA
                       organism = Cannabis sativa
SEQUENCE: 40
atcactgggt cagatcaaat gattnaaaaa caaaatcaaa attttctact            50

SEQ ID NO: 41          moltype = DNA  length = 50
FEATURE                Location/Qualifiers
misc_difference        25
                       note = t or a
source                 1..50
                       mol_type = genomic DNA
                       organism = Cannabis sativa
SEQUENCE: 41
agaaataaca tgtataaggc aagtnaagga aaagtacctg ttcctccatc            50

SEQ ID NO: 42          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 42
tcatataagt ttgctttgac ttttnattga tctcttatgc aaattattag            50

SEQ ID NO: 43          moltype = DNA  length = 50
FEATURE                Location/Qualifiers
misc_difference        25
                       note = t or c
source                 1..50
                       mol_type = genomic DNA
                       organism = Cannabis sativa
SEQUENCE: 43
aagcccaatt aaccacatta tgggntgcaa aattacaagt tctactaaca            50

SEQ ID NO: 44          moltype = DNA  length = 50
FEATURE                Location/Qualifiers
misc_difference        25
                       note = t or g
source                 1..50
                       mol_type = genomic DNA
                       organism = Cannabis sativa
SEQUENCE: 44
cttgacaaag agtttcattg tcttnttggg aaaaggtaga aatctgcctt            50

SEQ ID NO: 45          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 45
aacttcatta taagaaaagt cattntactt agaatctctg aaacataagt            50

SEQ ID NO: 46          moltype = DNA  length = 50
FEATURE                Location/Qualifiers
misc_difference        25
                       note = t or g
source                 1..50
                       mol_type = genomic DNA
                       organism = Cannabis sativa
SEQUENCE: 46
catttgagtg agaaaatcct caaantgagg aaagttgtca tgcatgatca            50
```

-continued

```
SEQ ID NO: 47          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 47
ttcactttgg ccatgacaag catanctagt caataaagta ttccaagaaa            50

SEQ ID NO: 48          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 48
tatttaaata ttattttcat attantttta tgtaattttc ttgttgtttt            50

SEQ ID NO: 49          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 49
acactttcta ggaaaacttc tcaanaagcc acccattctt tcgtcagagt            50

SEQ ID NO: 50          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 50
cagtgcggct gacctgaggt gtatnactac gcttgccaat taggatattt            50

SEQ ID NO: 51          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 51
attttcttcg tcttctttca caaanggaag gctgccgggg ctttcttcct            50

SEQ ID NO: 52          moltype = DNA  length = 50
FEATURE                Location/Qualifiers
misc_difference        25
                       note = c or a
source                 1..50
                       mol_type = genomic DNA
                       organism = Cannabis sativa
SEQUENCE: 52
caatttttc aattgaagcg gtttnacgtg tttgatgttt tggatgcatt             50

SEQ ID NO: 53          moltype = DNA  length = 50
FEATURE                Location/Qualifiers
misc_difference        25
                       note = t or g
source                 1..50
                       mol_type = genomic DNA
                       organism = Cannabis sativa
SEQUENCE: 53
ggccaaggct ccatatgaga gccangagca atggaaaaaa tttatatata            50

SEQ ID NO: 54          moltype = DNA  length = 50
FEATURE                Location/Qualifiers
misc_difference        25
                       note = c or g
source                 1..50
                       mol_type = genomic DNA
                       organism = Cannabis sativa
```

-continued

```
SEQUENCE: 54
actaggagat actgcagtta gtctnaatac agttgaagtg gaataggtag            50

SEQ ID NO: 55          moltype = DNA  length = 50
FEATURE                Location/Qualifiers
misc_difference        25
                       note = c or a
source                 1..50
                       mol_type = genomic DNA
                       organism = Cannabis sativa
SEQUENCE: 55
aacctctccc agggtcagcc tgatnctgat gtttgaggga agggtttggc            50

SEQ ID NO: 56          moltype = DNA  length = 50
FEATURE                Location/Qualifiers
misc_difference        25
                       note = a or t
source                 1..50
                       mol_type = genomic DNA
                       organism = Cannabis sativa
SEQUENCE: 56
atttgattca atgtctaata actcnggtga ttttttatgc cattcttagg            50

SEQ ID NO: 57          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 57
ttatagcaat taatatatgg tttanaaaca gtgaatatta aatattaata            50

SEQ ID NO: 58          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 58
aaaatgatca ttaaaccata tctancccat cagactcgct ctccctgctg            50

SEQ ID NO: 59          moltype = DNA  length = 50
FEATURE                Location/Qualifiers
misc_difference        25
                       note = t or g
source                 1..50
                       mol_type = genomic DNA
                       organism = Cannabis sativa
SEQUENCE: 59
gaccgcctcc catctcgacc ctatnaccct gactccttgt atttcgttgg            50

SEQ ID NO: 60          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 60
caacccagaa caacttaaga gtcantataa gcaagaattc aaacacaaaa            50

SEQ ID NO: 61          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 61
tacacttcat tttataaatg ataanactgt agaaacaatt gaaatttaga            50

SEQ ID NO: 62          moltype = DNA  length = 50
FEATURE                Location/Qualifiers
misc_difference        25
                       note = t or c
```

-continued

```
source                  1..50
                        mol_type = genomic DNA
                        organism = Cannabis sativa
SEQUENCE: 62
atcaagctaa atgggaaaac ttccnacaat agaaatcaag caattaattc            50

SEQ ID NO: 63           moltype = DNA  length = 50
FEATURE                 Location/Qualifiers
misc_difference         25
                        note = g or a
source                  1..50
                        mol_type = genomic DNA
                        organism = Cannabis sativa
SEQUENCE: 63
aggaaatagt acaaaagatt taatnaatat gtactgaaaa ttaatttcag            50

SEQ ID NO: 64           moltype = DNA  length = 50
FEATURE                 Location/Qualifiers
misc_difference         25
                        note = g or a
source                  1..50
                        mol_type = genomic DNA
                        organism = Cannabis sativa
SEQUENCE: 64
tcaaacaaca ttcaatctgt acaantgcat attttagatt tttcaatcca            50

SEQ ID NO: 65           moltype = DNA  length = 50
FEATURE                 Location/Qualifiers
misc_difference         25
                        note = a or g
source                  1..50
                        mol_type = genomic DNA
                        organism = Cannabis sativa
SEQUENCE: 65
ttatttagcc ctaatattat taatntagtt actgctgtta tatggggata            50

SEQ ID NO: 66           moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 66
attcatccaa aacttcctaa tcccnaaaag aaccgaatga atcaattgtg            50

SEQ ID NO: 67           moltype = DNA  length = 50
FEATURE                 Location/Qualifiers
misc_difference         25
                        note = a or g
source                  1..50
                        mol_type = genomic DNA
                        organism = Cannabis sativa
SEQUENCE: 67
tagcaagcaa agcatcttgg tcatntaaaa aaatcaccac atagcaaaag            50

SEQ ID NO: 68           moltype = DNA  length = 50
FEATURE                 Location/Qualifiers
misc_difference         25
                        note = g or t
source                  1..50
                        mol_type = genomic DNA
                        organism = Cannabis sativa
SEQUENCE: 68
atagggacat catctataat agtgngtatc tcttaaagaa aatgaaaata            50

SEQ ID NO: 69           moltype = DNA  length = 50
FEATURE                 Location/Qualifiers
misc_difference         25
                        note = g or a
source                  1..50
                        mol_type = genomic DNA
                        organism = Cannabis sativa
SEQUENCE: 69
tatttcagca aaaaagaaca tatantttta gtagcaggat caaccctgag            50
```

-continued

```
SEQ ID NO: 70          moltype = DNA  length = 50
FEATURE                Location/Qualifiers
misc_difference        25
                       note = a or c
source                 1..50
                       mol_type = genomic DNA
                       organism = Cannabis sativa
SEQUENCE: 70
atttaataat gtaaaatgat attanactat aagttatatt tgtataggtt            50

SEQ ID NO: 71          moltype = DNA  length = 50
FEATURE                Location/Qualifiers
misc_difference        25
                       note = c or a
source                 1..50
                       mol_type = genomic DNA
                       organism = Cannabis sativa
SEQUENCE: 71
tgactgtgca gcatagctta tgaantatca agagtgttag gatcccactc            50

SEQ ID NO: 72          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 72
gggacattga ggagatgatg aaatntggcg atattgcaaa atagcagcag            50

SEQ ID NO: 73          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 73
tattttttca gaactgattg tggcntttac ctcatcaaat ttgttgaatt            50

SEQ ID NO: 74          moltype = DNA  length = 50
FEATURE                Location/Qualifiers
misc_difference        25
                       note = a or c
source                 1..50
                       mol_type = genomic DNA
                       organism = Cannabis sativa
SEQUENCE: 74
agcgaggaga tatatcagat gcaanggtct aaaggtttgt ttaccatctc            50

SEQ ID NO: 75          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 75
tctgattata ttatgtactt attgntttgg tgtcaaatga ctcttccgat            50

SEQ ID NO: 76          moltype = DNA  length = 50
FEATURE                Location/Qualifiers
misc_difference        25
                       note = t or g
source                 1..50
                       mol_type = genomic DNA
                       organism = Cannabis sativa
SEQUENCE: 76
taagttgggc tttatctttc tattngaata ttctgtaagg ttctagatac            50

SEQ ID NO: 77          moltype = DNA  length = 50
FEATURE                Location/Qualifiers
misc_difference        25
                       note = a or g
source                 1..50
                       mol_type = genomic DNA
                       organism = Cannabis sativa
```

-continued

```
SEQUENCE: 77
atacaaatta gttactggca gaggnatttc aaattgagac aaggagaatt            50

SEQ ID NO: 78          moltype = DNA  length = 50
FEATURE                Location/Qualifiers
misc_difference        25
                       note = t or c
source                 1..50
                       mol_type = genomic DNA
                       organism = Cannabis sativa
SEQUENCE: 78
agtctcgatc tctccctcga actanaaaaa tcattgtaaa tatcgccttc            50

SEQ ID NO: 79          moltype = DNA  length = 50
FEATURE                Location/Qualifiers
misc_difference        25
                       note = t or a
source                 1..50
                       mol_type = genomic DNA
                       organism = Cannabis sativa
SEQUENCE: 79
tcatattaat ttagtcacaa aaaanttatg ttgtaattaa aagtagcctt            50

SEQ ID NO: 80          moltype = DNA  length = 50
FEATURE                Location/Qualifiers
misc_difference        25
                       note = t or c
source                 1..50
                       mol_type = genomic DNA
                       organism = Cannabis sativa
SEQUENCE: 80
tttcaccgaa aagtgaagat cgacntccat taagttttca acttcctgca            50

SEQ ID NO: 81          moltype = DNA  length = 50
FEATURE                Location/Qualifiers
misc_difference        25
                       note = a or t
source                 1..50
                       mol_type = genomic DNA
                       organism = Cannabis sativa
SEQUENCE: 81
ataccattca agatatctaa gctcngaagg aaatgatcag tctagaccat            50

SEQ ID NO: 82          moltype = DNA  length = 50
FEATURE                Location/Qualifiers
misc_difference        25
                       note = c or t
source                 1..50
                       mol_type = genomic DNA
                       organism = Cannabis sativa
SEQUENCE: 82
cttgtaacta aatatgattt ttagncacaa caaaaaatta cttgtaacta            50

SEQ ID NO: 83          moltype = DNA  length = 50
FEATURE                Location/Qualifiers
misc_difference        25
                       note = t or a
source                 1..50
                       mol_type = genomic DNA
                       organism = Cannabis sativa
SEQUENCE: 83
tgatctgagg gccactggga ggtcncccat ttgaactact acggccaaaa            50

SEQ ID NO: 84          moltype = DNA  length = 50
FEATURE                Location/Qualifiers
misc_difference        25
                       note = g or c
source                 1..50
                       mol_type = genomic DNA
                       organism = Cannabis sativa
SEQUENCE: 84
caattatttg agtcaataat caagntgcaa ctgctcttaa gctaccgatc            50

SEQ ID NO: 85          moltype = DNA  length = 50
FEATURE                Location/Qualifiers
misc_difference        25
                       note = g or c
```

-continued

```
source                  1..50
                        mol_type = genomic DNA
                        organism = Cannabis sativa
SEQUENCE: 85
aaatctttca aacacttgag gaagnatctc aatcatatta aatatctata            50

SEQ ID NO: 86           moltype = DNA  length = 50
FEATURE                 Location/Qualifiers
misc_difference         25
                        note = g or c
source                  1..50
                        mol_type = genomic DNA
                        organism = Cannabis sativa
SEQUENCE: 86
aaatttaatg acctggacta attangaact gccgcgtggc tattgacttc            50

SEQ ID NO: 87           moltype = DNA  length = 50
FEATURE                 Location/Qualifiers
misc_difference         25
                        note = c or g
source                  1..50
                        mol_type = genomic DNA
                        organism = Cannabis sativa
SEQUENCE: 87
ctgtaattat gtctagagta aatgnttgtg gatgagtatg caattgataa            50

SEQ ID NO: 88           moltype = DNA  length = 50
FEATURE                 Location/Qualifiers
misc_difference         25
                        note = t or c
source                  1..50
                        mol_type = genomic DNA
                        organism = Cannabis sativa
SEQUENCE: 88
cactctgtca ttccaaacac taacnccggt tctatgcagc atcctcccga            50

SEQ ID NO: 89           moltype = DNA  length = 50
FEATURE                 Location/Qualifiers
misc_difference         25
                        note = c or t
source                  1..50
                        mol_type = genomic DNA
                        organism = Cannabis sativa
SEQUENCE: 89
gaaatccatt aatagtaaat gcatncaatc taggatgtgc atctttagag            50

SEQ ID NO: 90           moltype = DNA  length = 50
FEATURE                 Location/Qualifiers
misc_difference         25
                        note = a or t
source                  1..50
                        mol_type = genomic DNA
                        organism = Cannabis sativa
SEQUENCE: 90
tgattcgcta aggaatgttt tggcntcgct atggcgtcca gggagaggaa            50

SEQ ID NO: 91           moltype = DNA  length = 50
FEATURE                 Location/Qualifiers
misc_difference         25
                        note = c or g
source                  1..50
                        mol_type = genomic DNA
                        organism = Cannabis sativa
SEQUENCE: 91
atcgtgtctt acaaggcgtg ggagngtata ttggaacgta tgttttctca            50

SEQ ID NO: 92           moltype = DNA  length = 50
FEATURE                 Location/Qualifiers
misc_difference         25
                        note = g or a
source                  1..50
                        mol_type = genomic DNA
                        organism = Cannabis sativa
SEQUENCE: 92
gccattccga aagattttgc cacanattgt ttgaggagtc cttggaaact            50
```

-continued

```
SEQ ID NO: 93          moltype = DNA  length = 50
FEATURE                Location/Qualifiers
misc_difference        25
                       note = a or t
source                 1..50
                       mol_type = genomic DNA
                       organism = Cannabis sativa
SEQUENCE: 93
tgacatggag ctaaggggtt atccntttac ttgggaaaaa gggaagggta             50

SEQ ID NO: 94          moltype = DNA  length = 50
FEATURE                Location/Qualifiers
misc_difference        25
                       note = a or t
source                 1..50
                       mol_type = genomic DNA
                       organism = Cannabis sativa
SEQUENCE: 94
gataaaaaag aaaggttgga ttggnacaat tgttgaaacc gattgtctaa             50

SEQ ID NO: 95          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 95
cttaacatag gaagattcaa ataantcttt accagataga ataaaacctc             50

SEQ ID NO: 96          moltype = DNA  length = 50
FEATURE                Location/Qualifiers
misc_difference        25
                       note = a or g
source                 1..50
                       mol_type = genomic DNA
                       organism = Cannabis sativa
SEQUENCE: 96
cacatttagc tgcacgaaat tgatnatgaa caataaaaat cagaattaca             50

SEQ ID NO: 97          moltype = DNA  length = 50
FEATURE                Location/Qualifiers
misc_difference        25
                       note = c or g
source                 1..50
                       mol_type = genomic DNA
                       organism = Cannabis sativa
SEQUENCE: 97
aaccaaaaag attacagaca tccantacta aaagcttatt aacttaattt             50

SEQ ID NO: 98          moltype = DNA  length = 50
FEATURE                Location/Qualifiers
misc_difference        25
                       note = g or a
source                 1..50
                       mol_type = genomic DNA
                       organism = Cannabis sativa
SEQUENCE: 98
tgttgatcaa ttttccagaa tattnattac ttttcatcac cccttataat             50

SEQ ID NO: 99          moltype = DNA  length = 50
FEATURE                Location/Qualifiers
misc_difference        25
                       note = a or t
source                 1..50
                       mol_type = genomic DNA
                       organism = Cannabis sativa
SEQUENCE: 99
gcattcaggt cattcacact aatgntggtc tattcttatc tcagcaaaaa             50

SEQ ID NO: 100         moltype = DNA  length = 50
FEATURE                Location/Qualifiers
misc_difference        25
                       note = g or c
source                 1..50
                       mol_type = genomic DNA
                       organism = Cannabis sativa
```

-continued

```
SEQUENCE: 100
ttctagcata gacagaagta taatncttga catgttttta aatgaaaact            50

SEQ ID NO: 101          moltype = DNA  length = 50
FEATURE                 Location/Qualifiers
misc_difference         25
                        note = t or a
source                  1..50
                        mol_type = genomic DNA
                        organism = Cannabis sativa
SEQUENCE: 101
agcatcattg atgttcttta gcatnttttt agggcacatt atttttttg             50
```

What is claimed is:

1. A new and distinct variety of *Cannabis* plant named 'Pure Red 3', substantially as illustrated and described herein.

* * * * *